(12) United States Patent
Boes

(10) Patent No.: US 7,919,503 B2
(45) Date of Patent: Apr. 5, 2011

(54) P2X7R ANTAGONISTS AND THEIR USE

(75) Inventor: Michael Boes, Munich (DE)

(73) Assignee: Affectis Pharmaceuticals AG, Martinsried (DE)

( * ) Notice: Subject to any disclaimer, the term of this patent is extended or adjusted under 35 U.S.C. 154(b) by 0 days.

(21) Appl. No.: 12/758,557

(22) Filed: Apr. 12, 2010

(65) Prior Publication Data

US 2010/0267762 A1    Oct. 21, 2010

(30) Foreign Application Priority Data

Apr. 14, 2009 (EP) .................................. 09005324
Mar. 11, 2010 (EP) .................................. 10156190

(51) Int. Cl.
*A61K 31/437* (2006.01)
*A61K 31/404* (2006.01)
*C07D 221/00* (2006.01)
*C07D 209/00* (2006.01)

(52) U.S. Cl. ......... 514/300; 514/415; 546/112; 548/469
(58) Field of Classification Search .................. 514/300, 514/415; 546/112; 548/469
See application file for complete search history.

(56) References Cited

U.S. PATENT DOCUMENTS

2006/0160879 A1 *   7/2006   Olofsson et al. .............. 514/414
* cited by examiner

*Primary Examiner* — Rebecca L Anderson
*Assistant Examiner* — Samantha L Shterengarts
(74) *Attorney, Agent, or Firm* — Cooley LLP

(57) ABSTRACT

The present application is directed to novel P2X7R antagonists that are N-indol-3-yl-acetamide and N-azaindol-3-yl-acetamide compounds, pharmaceutical compositions comprising the same and their use for the prophylactic or therapeutic treatment of diseases mediated by P2X7R activity.

12 Claims, 2 Drawing Sheets

P2X7R ANTAGONISTS AND THEIR USE

CROSS REFERENCE TO RELATED APPLICATIONS

This application claims priority to European Patent Application No. 09 00 5324.0, filed on Apr. 14, 2009 and European Patent Application No. 10 15 6190.0, filed on Mar. 11, 2010, which are herein incorporated by reference in their entirety.

FIELD OF INVENTION

The present application relates to novel P2X7R antagonists that are N-indol-3-yl-acetamide and N-azaindol-3-yl-acetamide compounds, pharmaceutical compositions comprising these compounds and to their use in the prophylactic and therapeutic treatment of diseases and disorders mediated by P2X7R.

BACKGROUND

P2X7R is an ATP-gated ion channel belonging to the P2X ionotropic channel family. The gene was first isolated from rat brain (Surprenant et al. (1996) 272:735-738) and subsequently from a human monocyte library (Rassendren et al. (1997) J. Biol. Chem. 272:5482-5486; Genbank accession numbers NM_002562, Y09561) by virtue of its sequence homology with the other members of the P2X family. It was later found that P2X7R corresponded to the unidentified P2Z receptor which mediates the permeabilising action of ATP on mast cells and macrophages (Dahlqvist and Diamant (1974) Acta Physiol. Scand. 34:368-384; Steinberg and Silverstein (1987) J. Biol. Chem. 262:3118-3122; Gordon (1986) Biochem. J. 233:309-319). The P2X7R has two hydrophobic membrane-spanning domains, an extracellular loop, and forms transmembrane ion channels. P2X7R bears a pharmacological profile markedly different from other P2X homo- or heteromers (North and Surprenant (2000) Annual Rev. Pharmacology Toxicology 40:563-580). P2X7R requires levels of ATP in excess of 1 mM to achieve activation, whereas other P2X receptors activate at ATP concentrations of $\leq 100$ μM (Steinberg et al. (1987) J. Biol. Chem. 262:8884-8888; Greenberg at al. (1988) J. Biol. Chem. 263:10337-10343). While all P2X receptors demonstrate non-selective channel-like properties following ligation, the channels formed by the P2X7R can rapidly transform into pores that can allow the passage of molecules of up to 900 Dalton (Virginio et al. (1999) J. Physiol. 519:335-346). P2X7R is expressed in haematopoietic cells, mast cells, lymphocytes, erythrocytes, fibroblast, Langerhans cells, and macrophages (Surprenant et al., 1996, Science 272:3118-3122). In the central nervous system, P2X7R expression has been reported in glial cells, Schwann cells, astrocytes, as well as in neurons (Ferrari et al. (1996) J. Immunol 156:1531-1539; Collo et al. (1997) Neuropharmacology 36: 1277-1283; Anderson and Nedergaard (2006) Trends Neuroscien 29: 257-262).

P2X7R is involved in the regulation of the immune function and inflammatory response. Activation of P2X7R by ATP in macrophages is associated with mitogenic stimulation of T cells (Baricordi et al. (1996) Blood 87:682-690), the release of cytokines (Griffiths et al. (1995) J. Immol. 154:2821-2828), and formation of macrophage polykarions (Falzon' et al. (1995) J. Clin. Invest. 95:1207-1216). P2X7R is involved in the processing and release of active interleukin-1beta (IL-1β) from proinflammatory cells (Perregaux and Gabel (1998) J Biol Chem 269:15195-15203; Ferrari et al., (2006) J Immunol 176: 3877-3883). Stimulation of the P2X7R by ATP can also result in apoptosis and cell death by triggering the formation of non-selective plasma membrane pores (Di Virgilio et al. (1998) Cell Death Differ. 5:191-199).

Upregulation of P2X7R has been observed during ischemic damage and necrosis induced by occlusion of middle cerebral artery in rat brain (Collo et al. (1997) Neuropharmacol 36:1277-1283). Recent studies indicate a role of P2X7R in the generation of superoxide in microglia, and upregulation of P2X7R has been detected around amyloid plaques in a transgenic mouse models for Alzheimer's disease (Parvathenani et al. (2003) J Biol Chem 278:13300-13317) and in multiple sclerosis lesions from autopsy brain sections (Narcisse et al. (2005) Glia, 49:245-258).

Studies from mice lacking P2X7R resulted in absence of inflammatory and neuropathic hypersensitivity to mechanical and thermal stimuli, indicating a link between P2X7R and inflammatory and neuropathic pain (Chessell et al. (2005) Pain 114:386-396). Antagonists of P2X7R significantly improved functional recovery and decreased cell death in spinal cord injury in animal models (Wang et al. (2004) Nature Med 10:B21-B27).

Compounds which modulate P2X7R have been reported. For example, Brilliant Blue (Jiang et al., Mol. Phamacol. 58 (2000), 82-88), the isoquinolines 1-[N,O-Bis(5-isoquinoline-sulfonyl)-N-methyl-L-tyrosyl]-4-phenylpiperazine and N-[1-[N-methyl-p-(5 isoquinolinesulfonyl)benzyl]-2-(4-phenylpiperazine)ethyl]-5-isoquinolinesulfonamide (Humphreys et al., Mol. Pharmacol., 54 (1998), 22-32), adamantane derivatives (WO 99/29660, WO 99/29661, WO 00/61569, WO 01/42194, WO 01/44170, WO 01/44213, WO 01/94338, WO 03/041707, WO 03/042190, WO 03/080579, WO 04/074224, WO 05/014529, WO 06/025783, WO 06/059945), piperidine and piperazine compounds (WO 01/44213, WO 01/46200, WO 08/005,368), benzamide and heteroarylamide compounds (WO 03/042191, WO 04/058731, WO 04/058270, WO 04/099146, WO 05/019182, WO 06/003500, WO 06/003513, WO 06/067444), substituted tyrosine derivatives (WO 00/71529, WO 03/047515, WO 03/059353), imidazole compounds (WO 05/014555), amino-tetrazoles compounds (WO 05/111003), cyanoamidine (WO 06/017406), bicycloheteroaryl derivatives (WO 05/009968, WO 06/102588, WO 06/102610, WO 07/028, 022, WO 07/109,154, WO 07/109,160, WO 07/109,172, WO 07/109,182, WO 07/109,192, WO 07/109,201), acylhydrazide (WO 06/110516), and other examples (WO 99/29686, WO 04/106305, WO 05/039590, WO 06/080884, WO 06/086229, WO 06/136004, WO 07/025,366, WO 07/056,046, WO 07/056,091, WO 07/141,267, WO 07/141, 269, WO 08/003,697) are antagonists of P2X7R while Oxidized ATP (oATP) acts as an irreversible inhibitor of the receptor (Chen et al., J. Biol. Chem., 268 (1993), 8199-8203).

Consequently, there is strong evidence that compounds acting on P2X7R can be used in the treatment of pain, inflammatory processes, and degenerative conditions associated with disease states such as rheumatoid arthritis, osteoarthritis, psoriasis, allergic dermatitis, asthma, chronic obstructive pulmonary disease, airways hyper-responsiveness, septic shock, glomerulonephritis, irritable bowel disease, inflammatory bowel disease, Crohn's disease, ulcerative colitis, atherosclerosis, growth and metastases of malignant cells, myoblastic leukaemia, diabetes, Alzheimer's disease, Parkinson's disease, multiple sclerosis, glaucoma, age-related macular degeneration, uveitis, neuropathic pain, depression, bipolar affective disorders, anxiety, meningitis, traumatic brain injury, acute spinal cord injury, neuropathic pain, osteoporosis, burn injury, ischemic heart disease, myocardial infarction, stroke, and varicose veins.

Thus, the object on the present invention is to provide a novel series of compound which can inhibit P2X7R activity and can be used in the treatment of the above mentioned diseases.

DETAILED DESCRIPTION OF THE INVENTION

Figure 1:
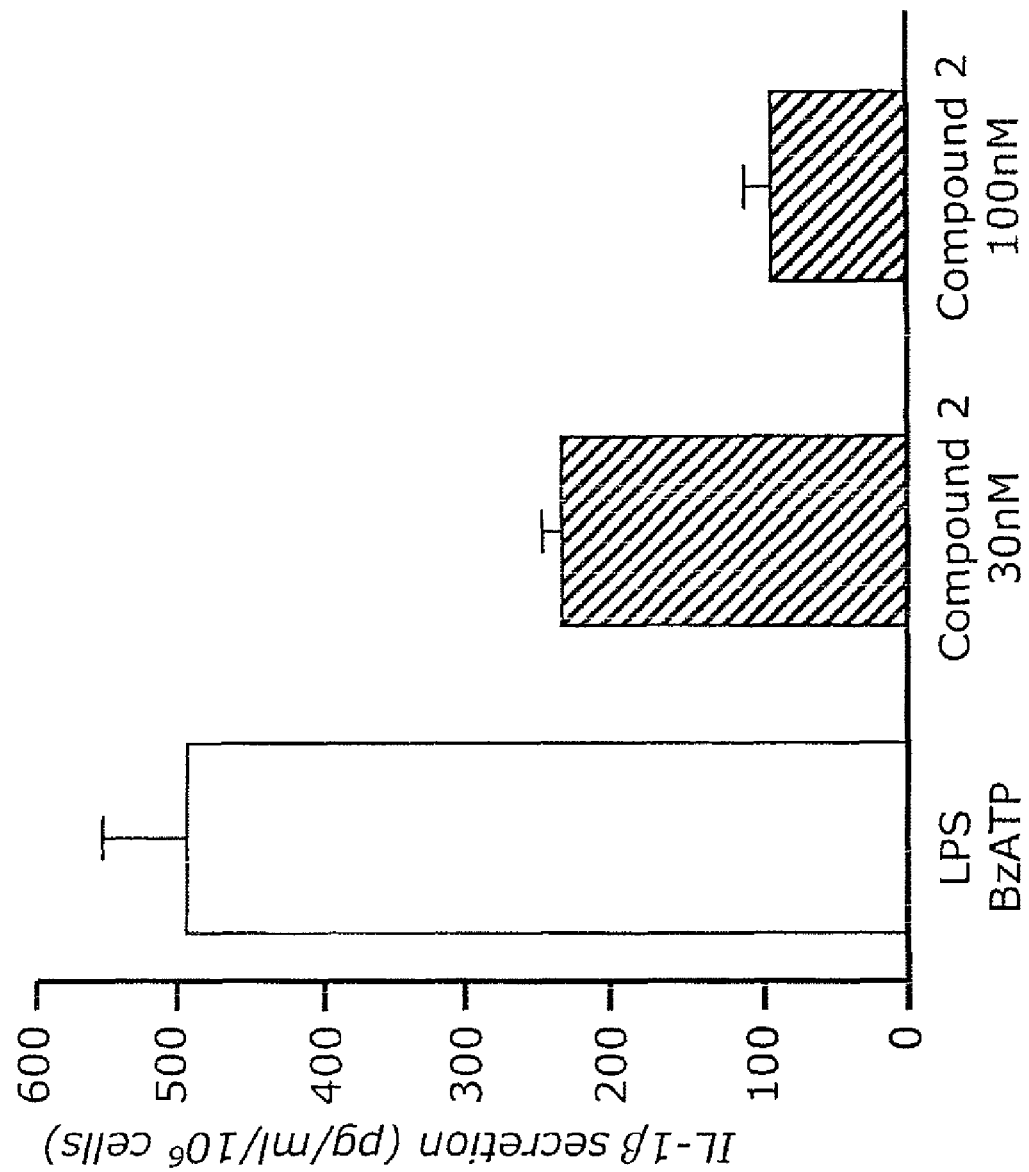
FIG. 1 discloses data showing the inhibition of IL-1beta secretion (* p<0.01) by compounds of the invention.

The present invention relates to novel P2X7R antagonists that are N-indol-3-yl-acetamide and N-azaindol-3-yl-acetamide compounds represented by the general formula (I):

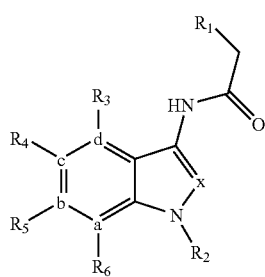

wherein,
$R_1$ is a mono- or bicycloalkylalkyl group or mono- or bicycloalkyl group;
$R_2$ is selected from straight or branched $C_1$-$C_5$ alkyl which may optionally substituted with —OH, —CH$_2$—OH, $C_1$-$C_5$ alkoxy, NH$_2$—, N(R$_a$)$_2$—, NHR$_a$—, CN—, CF$_3$, halogen (i.e. Cl, F, Br or I), piperidino, morpholine, pyrrolidino, 5H-tetrazolylpropyl, methylcarbamoyl, dimethylcarbamoyl, or ethylmethylcarbamoyl, wherein $R_a$ is $C_1$-$C_5$ alkyl;
$R_3$, $R_4$, $R_5$, $R_6$ are at each occurrence independently selected from hydrogen, halogen (i.e. Cl, F, Br or I), methyl, methoxy, cyano, or trifluoromethyl;
a, b, c, d, x are at each occurrence independently selected from carbon, or nitrogen; or a pharmaceutically acceptable salt or solvate thereof (whereby x must have a hydrogen substituent if it is carbon).

Compounds of Formula (I), wherein $R_1$ is a group selected from cyclopentyl, cyclopentylmethyl, cyclohexyl, cyclohexylmethyl, cycloheptyl, cycloheptylmethyl, bicyclo[2.2.2]octan-1-yl and bicyclo[2.2.2]octan-1-ylmethyl are preferred.

Preferred are also compounds, wherein $R_2$ is substituted with one or two substituents selected from —OH, —CH$_2$—OH, $C_1$-$C_5$ alkyl, —NH$_2$, NHRa, —CN, —CF$_3$, halogen, piperidino, morpholino, pyrrolidino or 5H-tetrazolylpropyl.

Compounds as disclosed above, wherein $R_2$ is $C_1$-$C_5$ alkyl or $C_2$-$C_5$ hydroxyalkyl are also preferred.

Furthermore, it is preferred that at least two of $R_3$, $R_4$, $R_5$ and $R_6$ are hydrogen. If necessitated by valency, $R_3$-$R_6$ may also be absent.

Additionally, it is preferred that a, b, c, and d are C or one of a, b, c and d is N.

Examples of novel N-indol-3-yl-acetamide and N-azaindol-3-yl-acetamide compounds are disclosed in examples 1-3.

The invention further relates to a compound of Formula (I) or a pharmaceutically acceptable salt or solvate thereof, being:
N-(4-chloro-1-(2-hydroxyethyl)-1H-indol-3-yl)-2-cycloheptylacetamide,
N-(4-bromo-1-(2-hydroxyethyl)-1H-indol-3-yl)-2-cycloheptylacetamide,
N-(4-chloro-1-(2-hydroxyethyl)-1H-indol-3-yl)-2-cyclohexylacetamide,
N-(4-bromo-1-(2-hydroxyethyl)-1H-indol-3-yl)-2-cyclohexylacetamide,
N-(4-chloro-1-(2-hydroxypropyl)-1H-indol-3-yl)-2-cycloheptylacetamide,
N-(4-bromo-1-(2-hydroxypropyl)-1H-indol-3-yl)-2-cycloheptylacetamide,
N-(4-chloro-1-(hydroxymethyl)-1H-indol-3-yl)-3-cyclohexylpropanamide,
N-(4-bromo-1-(hydroxymethyl)-1H-indol-3-yl)-3-cyclohexylpropanamide,
N-(4-chloro-1-(hydroxymethyl)-1H-indol-3-yl)-3-cycloheptylpropanamide,
N-(4-bromo-1-(hydroxymethyl)-1H-indol-3-yl)-3-cycloheptylpropanamide,
N-(4-chloro-1-(2-hydroxyethyl)-1H-pyrrolo[2,3-b]pyridin-3-yl)-2-cyclohexylacetamide,
N-(4-bromo-1-(2-hydroxyethyl)-1H-pyrrolo[2,3-b]pyridin-3-yl)-2-cyclohexylacetamide,
N-(4-chloro-1-(2-hydroxyethyl)-1H-pyrrolo[2,3-b]pyridin-3-yl)-2-cycloheptylacetamide,
N-(4-bromo-1-(2-hydroxyethyl)-1H-pyrrolo[2,3-b]pyridin-3-yl)-2-cycloheptylacetamide,
N-(4-chloro-1-(2-hydroxypropyl)-1H-pyrrolo[2,3-b]pyridin-3-yl)-2-cycloheptylacetamide,
N-(4-bromo-1-(2-hydroxypropyl)-1H-pyrrolo[2,3-b]pyridin-3-yl)-2-cycloheptylacetamide,
N-(4-chloro-1-(2-hydroxyethyl)-1H-pyrrolo[2,3-b]pyridin-3-yl)-3-cyclohexylpropanamide, and
N-(4-bromo-1-(2-hydroxyethyl)-1H-pyrrolo[2,3-b]pyridin-3-yl)-3-cyclohexylpropanamide.
N-(4-chloro-1-(2-hydroxypropyl)-1H-indol-3-yl)-2-cyclohexylacetamide,
N-(4-bromo-1-(2-hydroxypropyl)-1H-indol-3-yl)-2-cyclohexylacetamide,
2-(bicyclo[2.2.2]octan-1-yl)-N-(4-chloro-1-(2-hydroxypropyl)-1H-indol-3-yl)acetamide,
2-(bicyclo[2.2.2]octan-1-yl)-N-(4-bromo-1-(2-hydroxypropyl)-1H-indol-3-yl)acetamide,
N-(4-chloro-1-(2-hydroxypropyl)-1H-indol-3-yl)-3-cyclohexylpropanamide,
N-(4-bromo-1-(2-hydroxypropyl)-1H-indol-3-yl)-3-cyclohexylpropanamide,
N-(4-chloro-1-(2-hydroxypropyl)-1H-indol-3-yl)-3-cycloheptylpropanamide,
N-(4-bromo-1-(2-hydroxypropyl)-1H-indol-3-yl)-3-cycloheptylpropanamide,
N-(4-chloro-1-(1,3-dihydroxypropan-2-yl)-1H-indol-3-yl)-2-cyclohexylacetamide,
N-(4-bromo-1-(1,3-dihydroxypropan-2-yl)-1H-indol-3-yl)-2-cyclohexylacetamide,
N-(4-chloro-1-(1,3-dihydroxypropan-2-yl)-1H-indol-3-yl)-2-cycloheptylacetamide,
N-(4-bromo-1-(1,3-dihydroxypropan-2-yl)-1H-indol-3-yl)-2-cycloheptylacetamide,
2-(bicyclo[2.2.2]octan-1-yl)-N-(4-chloro-1-(1,3-dihydroxypropan-2-yl)-1H-indol-3-yl)acetamide
2-(bicyclo[2.2.2]octan-1-yl)-N-(4-bromo-1-(1,3-dihydroxypropan-2-yl)-1H-indol-3-yl)acetamide, N-(4-chloro-1-(1,3-dihydroxypropan-2-yl)-1H-indol-3-yl)-3-cyclohexylpropanamide,
N-(4-bromo-1-(1,3-dihydroxypropan-2-yl)-1H-indol-3-yl)-3-cyclohexylpropanamide,
N-(4-chloro-1-(1,3-dihydroxypropan-2-yl)-1H-indol-3-yl)-3-cycloheptylpropanamide,
N-(4-bromo-1-(1,3-dihydroxypropan-2-yl)-1H-indol-3-yl)-3-cycloheptylpropanamide,
N-(1-(3-amino-2-hydroxypropyl)-4-chloro-1H-indol-3-yl)-2-cyclohexylacetamide,
N-(1-(3-amino-2-hydroxypropyl)-4-bromo-1H-indol-3-yl)-2-cyclohexylacetamide,
N-(1-(3-amino-2-hydroxypropyl)-4-chloro-1H-indol-3-yl)-2-cycloheptylacetamide,
N-(1-(3-amino-2-hydroxypropyl)-4-bromo-1H-indol-3-yl)-2-cycloheptylacetamide,
N-(1-(3-amino-2-hydroxypropyl)-4-chloro-1H-indol-3-yl)-2-(bicyclo[2.2.2]octan-1-yl)acetamide,
N-(1-(3-amino-2-hydroxypropyl)-4-bromo-1H-indol-3-yl)-2-(bicyclo[2.2.2]octan-1-yl)acetamide,
N-(1-(3-amino-2-hydroxypropyl)-4-chloro-1H-indol-3-yl)-3-cyclohexylpropanamide,
N-(1-(3-amino-2-hydroxypropyl)-4-bromo-1H-indol-3-yl)-3-cyclohexylpropanamide,
N-(1-(3-amino-2-hydroxypropyl)-4-chloro-1H-indol-3-yl)-3-cycloheptylpropanamide,
N-(1-(3-amino-2-hydroxypropyl)-4-bromo-1H-indol-3-yl)-3-cycloheptylpropanamide,
N-(4-chloro-1-methyl-1H-indol-3-yl)-2-cyclohexylacetamide,
N-(4-bromo-1-methyl-1H-indol-3-yl)-2-cyclohexylacetamide,
N-(4-chloro-1-methyl-1H-indol-3-yl)-2-cycloheptylacetamide,
N-(4-bromo-1-methyl-1H-indol-3-yl)-2-cycloheptylacetamide,
2-(bicyclo[2.2.2]octan-1-yl)-N-(4-chloro-1-methyl-1H-indol-3-yl)acetamide,
2-(bicyclo[2.2.2]octan-1-yl)-N-(4-bromo-1-methyl-1H-indol-3-yl)acetamide,
N-(4-chloro-1-methyl-1H-indol-3-yl)-3-cyclohexylpropanamide,
N-(4-bromo-1-methyl-1H-indol-3-yl)-3-cyclohexylpropanamide,
N-(4-chloro-1-methyl-1H-indol-3-yl)-3-cycloheptylpropanamide,
N-(4-bromo-1-methyl-1H-indol-3-yl)-3-cycloheptylpropanamide,
N-(4-chloro-1-(2-hydroxy-3-(methylamino)propyl)-1H-indol-3-yl)-2-cyclohexylacetamide,
N-(4-bromo-1-(2-hydroxy-3-(methylamino)propyl)-1H-indol-3-yl)-2-cyclohexylacetamide,
N-(4-chloro-1-(2-hydroxy-3-(methylamino)propyl)-1H-indol-3-yl)-2-cycloheptylacetamide,
N-(4-bromo-1-(2-hydroxy-3-(methylamino)propyl)-1H-indol-3-yl)-2-cycloheptylacetamide,
2-(bicyclo[2.2.2]octan-1-yl)-N-(4-chloro-1-(2-hydroxy-3-(methylamino)propyl)-1H-indol-3-yl)acetamide, and
2-(bicyclo[2.2.2]octan-1-yl)-N-(4-bromo-1-(2-hydroxy-3-(methylamino)propyl)-1H-indol-3-yl)acetamide.

The present invention also includes isotopically-labelled compounds, which are identical to those recited in Formula (I), but for the fact that one or more atoms are replaced by an atom having an atomic mass or mass number different from the atomic mass or mass 25 number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{35}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances.

Isotopically-labelled compounds of Formula (I) of this invention and prodrugs thereof can generally be prepared by carrying out the procedures disclosed in the Examples below, by substituting a readily available isotopically-labelled reagent for a non-isotopically-labelled reagent.

Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine and procaine.

Further Pharmaceutically Acceptable Salts

In an further embodiment the present application is directed to a pharmaceutical composition comprising a compound of Formula (I) of the present invention.

The pharmaceutical composition according to the present invention may further comprise an additional active compound in separate or unit dosage form for simultaneous or sequential administration.

The compounds of Formula (I) or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cells, such as but not limited to monocytes and/or macrophages.

The present invention also relates to the treatment of an IL-1 or cytokine mediated condition.

As defined herein, an "IL-1 mediated condition" and "cytokine mediated condition" includes, but is not limited to, a disease or disorder selected from the group consisting of arthritis (including psoriatic arthritis, Reiter's syndrome, rheumatoid arthritis, gout, traumatic arthritis, rubella arthritis, rheumatoid spondylitis, osteoarthritis, gouty arthritis and acute synovitis), inflammatory bowel disease, Crohn's disease, emphysema, acute respiratory distress syndrome, adult respiratory distress syndrome, asthma, bronchitis chronic obstructive pulmonary disease, chronic pulmonary inflammatory disease, silicosis, pulmonary sarcoidosis, allergic reactions, allergic contact hypersensitivity, eczema, contact dermatitis, psoriasis, sunburn, cancer, tissue ulceration, restenosis, periodontal disease, epidermolysis bullosa, osteoporosis, bone resorption disease, loosening of artificial joint implants, atherosclerosis, aortic aneurysm, congestive heart failure, myocardial infarction, stroke, cerebral ischemia, head trauma, neurotrauma, spinal cord injury, neuro-degenerative disorders, Alzheimer's disease, Parkinson's disease, glaucoma, age-related macular degeneration, uveitis, neuropathic pain, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, corneal scarring, scleritis, abnormal wound healing, burns, autoimmune disorders, Huntington's disease, diabetes, AIDS, cachexia, sepsis, septic shock, endotoxic shock, conjunctivitis shock, gram negative sepsis, toxic shock syndrome, cerebral malaria, cardiac and renal reperfusion injury, thrombosis, glomerularonephritis, graft vs. host reaction, allograft rejection, organ transplant toxicity, ulcerative colitis, or muscle degeneration, in a mammal, including a human, comprising administering to said mammal an amount of a compound to Formula (I), effective in treating such a condition.

The present invention relates to a pharmaceutical composition for the treatment of an IL-1 mediated condition in a mammal, including a human, comprising an amount of a compound of Formula (I), effective in treating such a condition and a pharmaceutically acceptable carrier.

The compounds of the invention are useful for the treatment of rheumatoid arthritis, osteoarthritis, psoriasis, allergic dermatitis, asthma, chronic obstructive pulmonary disease (COPD), hyperresponsiveness of the airway, septic shock, glomerulonephritis, irritable bowel disease, Crohn's disease, ulcerative colitis, atherosclerosis, growth and metastases of malignant cells, myoblastic leukemia, diabetes, Alzheimer's disease, meningitis, osteoporosis, burn injury, ischemic heart disease, stroke and varicose veins.

In another aspect, the invention further provides a pharmaceutical composition for treating osteoarthritis which comprises a therapeutically effective amount of a compound of Formula (I), or a pharmaceutically acceptable salt or solvate thereof, as hereinbefore defined.

The invention further provides a pharmaceutical composition for effecting immunosuppression (e.g. in the treatment of rheumatoid arthritis, irritable bowel disease, atherosclerosis or psoriasis) which comprises a therapeutically effective amount of a compound of Formula (I), or a pharmaceutically acceptable salt or solvate thereof, as hereinbefore defined.

The invention also provides a pharmaceutical composition for treating an obstructive airways disease (e.g. asthma or COPD) which comprises a therapeutically effective amount of a compound of Formula (I), or a pharmaceutically acceptable salt or solvate thereof, as hereinbefore defined.

The present invention yet further provides a pharmaceutical composition for treating a mammal susceptible to or afflicted with conditions that are causally related to abnormal activity of the P2X7 receptor, such as neurodegenerative diseases and disorders including, for example, Parkinson's disease, multiple sclerosis, glaucoma, age-related macular degeneration, uveitis, neuropathic pain, diseases and disorders which are mediated by or result in neuroinflammation such as, for example traumatic brain injury and encephalitis; centrally-mediated neuropsychiatric diseases and disorders such as, for example depression mania, bipolar disease, anxiety, schizophrenia, eating disorders, sleep disorders and cognition disorders, epilepsy and seizure disorders comprising a therapeutically effective amount of a compound of Formula (I), or a pharmaceutically acceptable salt or solvate thereof, as hereinbefore defined.

In particular embodiment the pharmaceutical composition according to the present invention may be used for the treatment of affective disorders. In a preferred embodiment the affective disorder is selected from depression, anxiety, bipolar disorder and schizophrenia.

In an alternative embodiment the pharmaceutical composition according to the present invention is useful for the treatment of neurodegenerative diseases and disorders, diseases and disorders which are mediated by or result in neuroinflammation and centrally-mediated neuropsychiatric diseases and disorders.

Furthermore, the pharmaceutical composition according to the present invention may particularly be useful for the treatment of pain, inflammatory processes, and degenerative conditions. In a more preferred embodiment the inflammatory process is selected from rheumatoid arthritis, osteoporosis and chronic obstructive pulmonary disease.

Moreover, the pharmaceutical composition according to the present invention may be used for the treatment of neuropathic pain.

Dosage, pharmaceutical preparation and delivery of a compound of Formula (I) for use in accordance with the present invention can be formulated in conventional manner according to methods found in the art, using one or more physiological carriers or excipient, see, for example Ansel et al., "Pharmaceutical Dosage Forms and Drug Delivery Systems", 7th edition, Lippincott Williams & Wilkins Publishers, 1999. Thus, the P2X7R modulating agent and its physiologically acceptable salts and solvates can be formulated for administration by inhalation, insufflation (either through the mouth, or nose), oral, buccal, parenteral, or rectal administration. For oral administration, the pharmaceutical composition of a compound of Formula (I) can take the form of, for example, tablets or capsules prepared by conventional means with pharmaceutical acceptable excipients such as binding agents (e.g., pregelatinised maize starch, polyvinylpyrrolidone, hydroxypropyl methylcellulose), fillers (e.g., lactose, microcrystalline cellulose, calcium hydrogen phosphate), lubricants (e.g., magnesium stearate, talc, silica), disintegrants (e.g., potato starch, sodium starch glycolate), or wetting agents (e.g., sodium lauryl sulphate). The pharmaceutical composition can be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium ion, dried skim milk, glycerol, propylene, glycol, water, ethanol and the like. The composition, if desired, can also contain minor amounts of wetting or emulsifying agents, or pH buffering agents. These compositions can be in the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the aforementioned compounds, preferably in purified form, together with a suitable amount of carrier so as to provide the form for proper administration to the patient. The formulation should suit the mode of administration.

Liquid preparations for oral administration can be in the form of, for example, solutions, syrups, or suspensions, or can be presented as a dry product for constitution with water or other suitable vehicle before use. Such liquid preparation can be prepared by conventional means with pharmaceutically acceptable additives such as suspending agents (e.g., sorbitol, syrup, cellulose derivatives, hydrogenated edible fats), emulsifying agents (e.g., lecithin, acacia), non-aqueous vehicles (e.g., almond oil, oily esters, ethyl alcohol, fractionated vegetable oils), preservatives (e.g., methyl or propyl-p-hydroxycarbonates, soric acids). The preparations can also contain buffer salts, flavouring, coloring and sweetening agents as deemed appropriate. Preparations for oral administration can be suitably formulated to give controlled release of a compound of Formula (I).

For administration by inhalation, a compound of Formula (I) of the present invention is conveniently delivered in the form of an aerosol spray presentation from a pressurised pack or a nebulizer, with the use of a suitable propellant (e.g., dichlorodifluoromethane, trichlorofluoromethane, dichlorotetrafluoroethane, carbon dioxide or other suitable gas). In the case of a pressurised aerosol, the dosage unit can be determined by providing a valve to deliver a metered amount. Capsules and cartridges of, for example, gelatine, for use in an inhaler or insufflator can be formulated containing a powder mix of a compound of Formula (I) and a suitable powder base such as lactose or starch.

A compound of Formula (I) of the present invention can be formulated for parenteral administration by injection, for example, by bolus injection or continuous infusion. Site of injections include intra-venous, intra-peritoneal or sub-cutaneous. Formulations for injection can be presented in units dosage form (e.g., in phial, in multi-dose container), and with an added preservative. A compound of Formula (I) of the present invention can take such forms as suspensions, solutions or emulsions in oily or aqueous vehicles, and can contain formulatory agents such as suspending, stabilizing, or dispersing agents. Alternatively, the agent can be in powder form for constitution with a suitable vehicle (e.g., sterile pyrogen-free water) before use. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

A compound of Formula (I) of the present invention can be formulated for transdermal administration. Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base.

Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention. The compounds of this invention can also be administered by a transdermal device. Accordingly, transdermal administration can be accomplished using a patch either of the reservoir or porous membrane type, or of a solid matrix variety.

The pharmaceutical composition of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

A compound of Formula (I) of the present invention can also, if desired, be presented in a pack, or dispenser device which can contain one or more unit dosage forms containing the said agent. The pack can for example comprise metal or plastic foil, such as blister pack. The pack or dispenser device can be accompanied with instruction for administration.

A compound of Formula (I) of the present invention can be administered as sole active agent or can be adminstered in combination with other agents. These agents include nonsteroidal anti-inflammatory drug (NSAIDS) such as celecoxib, rofecoxib, cimicoxib, etoricoxib, lumiracoxib, valdecoxib, deracoxib, N-(2-cyclohexyloxynitrophenyl)methane sulphonamide, COX189, ABT963, JTE-522, GW-406381, LAS-34475, CS-706, PAC-10649, SVT-2016, GW-644784, tenidap, acetylsalicylic acid (aspirin), amoxiprin, benorilate, choline magnesium salicylate, diflunisal, faislamine, methyl salicylate, magnesium salicylate, salicyl salicylate (salsalatee), diclofenac, aceclofenac, acemetacin, bromfenac, etodolac, indometacin, nabumetone, sulindac, tolmetin, ibuprofen, carprofen, fenbufen, fenoprofen, flurbiprofen, ketoprofen, ketorolac, loxoprofen, naproxen, oxaprozin, tiaprofenic acid, suprofen, mefenamic acid, meclofenamic acid, phenylbutazone, azapropazone, metamizole, oxyphenbutazone, sulfinpyrazone, piroxicam, lornoxicam, meloxicam, tenoxicam, nimesulide, licofelone, paracetamol.

A compound of Formula (I) of the present invention can be combined with agents such as TNF-$\alpha$ inhibitors such as anti-TNF monoclonal antibodies (such as Remicade, CDP-870 and D2E7) and TNF receptor immunoglobulin molecules (such as Enbrel), low dose methotrexate, lefunomide; ciclesonide; hydroxychloroquine, d-penicillamine, auranofin or parenteral or oral gold.

A compound of Formula (I) of the present invention can also be administered in combination with an inhibitor of proTNFalpha convertase enzyme (TACE) such as 3-Amino-N-hydroxy-$\alpha$-(2-methylpropyl)-3-[4-[(2-methyl-4-quinolinyl)methoxy]phenyl]-2-oxo-1-pyrrolidineacetamide, 2(S), 3(S)-Piperidinedicarboxamide, N3-hydroxy-1-methyl-N-2-[4-[(2-methyl-4-quinolinyl)methoxy]phenyl], 3-Thiomorpholinecarboxamide, 4-[[4-(2-butynyloxy)phenyl]sulfonyl]-N-hydroxy-2,2-dimethyl, 5-Hexenoic acid, 3-[(hydroxyamino)carbonyl]-2-(2-methylpropyl)-6-phenyl-, 2-(2-methylpropyl)-2-(methylsulfonyl)hydrazide, (2R,3S, 5E), 2-Piperidinecarboxamide, N,5-dihydroxy-1-[[4-(1-naphthalenylmethoxy)phenyl]sulfonyl]-, (2R,5R), Pentanamide, 3-(formylhydroxyamino)-4-methyl-2-(2-methylpropyl)-N-[(1S,2S)-2-methyl-1-[(2-pyridinylamino) carbonyl]butyl]-, (2R,3S),2-Propenamide, N-hydroxy-3-[3-

[[(4-methoxyphenyl)sulfonyl](1-methylethyl)amino] phenyl]-3-(3-pyridinyl)-, (2E), Benzamide, N-(2,4-dioxo-1, 3,7-triazaspiro[4.4]non-9-yl)-4-[(2-methyl-4-quinolinyl) methoxy], Benzamide, N-[(1-acetyl-4-pipendinyl)(2,5-dioxo-4-imidazolidinyl)methyl]-4-[(2-meth-yl-4-quinolinyl)methoxy], or 2,4-imidazolidinedione, 5-methyl-5-[[[4-[(2-methyl-4-quinolinyl)methoxy]phenyl]sulfonyl] methyl]. Other examples of TACE inhibitors are described in WO 99/18074, WO 99/65867, U.S. Pat. No. 6,225,311, WO 00/00465, WO 00/09485, WO 98/38179, WO 02/18326, WO 02/096426, WO 03/079986, WO 03/055856, WO 03/053941, WO 03/040103, WO 03/031431. WO 03/024899, WO 03/016248, WO 04/096206, WO 04/033632, WO 04/108086, WO 04/043349, WO 04/032846, WO 04/012663, WO 04/006925, WO 07/016,597.

A compound of Formula (I) of the present invention can also be administered in combination with a corticosteroid such as budesonide, corticosterone, cortisol, cortisone acetate, prednisone, prednisolone, methylprednisolone, dexamethasone, betamethasone, triamcinolone, beclometasone, fludrocortisone acetate, deoxycorticosterone acetate (doca), aldosterone.

A compound of Formula (I) of the present invention can further be administered in combination with a β2-adrenergic receptor agonist such as formoterol, salbutamol (albuterol), levalbuterol, terbutaline, pirbuterol, procaterol, metaproterenol, fenoterol, bitolterol mesylate, salmeterol, bambuterol, clenbuterol.

A compound of Formula (I) of the present invention can further be administered in combination with an antidepressant drug such as sertraline, escitalopram, fluoxetine, bupropion, paroxetine, venlafaxine, trazodone, amitriptyline, citalopram, duloxetine, mirtazapine, nortriptyline, imipramine, lithium.

A compound of Formula (I) of the present invention can further be administered in combination with an antipsychotic drug such as chlorpromazine, fluphenazine, perphenazine, prochlorperazine, thioridazine, trifluoperazine, mesoridazine, promazine, triflupromazine, levomepromazine, promethazine, chlorprothixene, flupenthixol, thiothixene, zuclopenthixol, haloperidol, droperidol, pimozide, melperone, benperidol, triperidol, clozapine, olanzapine, risperidone, quetiapine, ziprasidone, amisulpride, paliperidone, bifeprunox, aripiprazole.

A compound of Formula (I) of the present invention can also be administered in combination with a leukotriene biosynthesis inhibitor, 5-lipoxygenase (5-LO) inhibitor or 5-lipoxygenase activating protein (FLAP) antagonist, for example, zileuton; ABT-761; fenleuton; tepoxalin; nicaraven; VIA-2291; etalocib; ketoprofen, Abt-79175; Abt-85761; N-(5-substituted) thiophene-2-alkylsulfonamides; TDT-070; licofelone; PEP-03; tenoxicam; 2,6-di-tert-butylphenol hydrazones; methoxytetrahydropyrans such as Zeneca ZD-2138; the compound SB-210661; pyridinyl-substituted 2-cyanonaphthalene compounds such as L-739-010; 2-cyanoquinoline compounds such as L-746-530; indole and quinoline compounds such as MK-591, MK-886, and BAY x 1005.

A compound of Formula (I) of the present invention can be administered in combination with a receptor antagonists for leukotrienes LTB4, LTC4, LTD4, and LTE, for example, phenothiazin-3-ones such as L-651,392; amidino compounds such as CGS-25019c; benzoxalamines such as ontezolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195; masilukast.

A compound of Formula (I) of the present invention can also be administered in combination with a PDE4 inhibitor including inhibitors of the isoform PDE4D.

A compound of Formula (I) of the present invention can also be administered in combination with a antihistaminic $H_1$ receptor antagonists including cetirizine, loratadine, desloratadine, fexofenadine, astemizole, azelastine, and chlorpheniramine.

A compound of Formula (I) of the present invention can further be administered in combination with a gastroprotective $H_2$ receptor antagonist.

A compound of Formula (I) of the present invention can yet further be administered in combination with an α1- and α2-adrenoceptor agonist vasoconstrictor sympathomimetic agent, including propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

A compound of Formula (I) of the present invention can be administered in combination with anticholinergic agents including ipratropium bromide; tiotropium bromide; oxitropium bromide; pirenzepine; and telenzepine The present invention still further relates to the combination of a compound of the invention together with a $β_1$- to $β_4$-adrenoceptor agonists including metaproterenol, isoproterenol, isoprenaline, albuterol, salbutamol; formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

A compound of Formula (I) of the present invention can be administered in combination with an insulin-like growth factor type I (IGF-1) mimetic.

A compound of Formula (I) of the present invention can be administered in combination with an inhaled glucocorticoid with reduced systemic side effects, including, prednisone, prednisolone, flunisolide, triamcinolone acetonide, beclomethasone dipropionate, budesonide, fluticasone propionate, and mometasone furoate.

A compound of Formula (I) of the present invention can be administered in combination with (a) tryptase inhibitors; (b) platelet activating factor (PAF) antagonists; (c) interleukin converting enzyme (ICE) inhibitors; (d) IMPDH inhibitors; (e) adhesion molecule inhibitors including VLA-4 antagonists; (f) cathepsins; (g) MAP kinase inhibitors; (h) glucose-6 phosphate dehydrogenase inhibitors; (i) kinin-$B_1$- and $B_2$-receptor antagonists; j) anti-gout agents, e.g., colchicine; (k) xanthine oxidase inhibitors, e.g., allopurinol; (l) uricosuric agents, e.g., probenecid, sulfinpyrazone, and benzbromarone; (m) growth hormone secretagogues; (n) transforming growth factor (TGFβ); (o) platelet-derived growth factor (PDGF); (p) fibroblast growth factor, e.g., basic fibroblast growth factor (bFGF); (q) granulocyte macrophage colony stimulating factor (GM-CSF); (r) capsaicin cream; (s) Tachykinin $NK_1$ and $NK_3$ receptor antagonists such as NKP-608C; SB-233412 (talnetant); and D-4418; and (t) elastase inhibitors such as UT-77 and ZD-0892.

A compound of Formula (I) of the present invention can be administered in combination with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11).

A compound of Formula (I) of the present invention can be administered in combination with anticancer agents such as endostatin and angiostatin or cytotoxic drugs such as adriamycin, daunomycin, cis-platinum, etoposide, taxol, taxotere and farnesyl transferase inhibitors, VEGF inhibitors, COX-2 inhibitors and antimetabolites such as methotrexate antineoplastic agents, especially antimitotic drugs including the vinca alkaloids such as vinblastine and vincristine.

A compound of Formula (I) of the present invention can be administered in combination with antiviral agents such as Viracept, AZT, aciclovir and famciclovir, and antisepsis compounds such as Valant.

A compound of Formula (I) of the present invention can be administered in combination with cardiovascular agents such as calcium channel blockers, lipid lowering agents such as statins, fibrates, beta-blockers, ACE inhibitors, Angiotensin-2 receptor antagonists and platelet aggregation inhibitors.

A compound of Formula (I) of the present invention can be administered in combination with CNS agents such as anti-depressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metrifonate.

A compound of Formula (I) of the present invention can be administered in combination with osteoporosis agents such as roloxifene, droloxifene, lasofoxifene or fosomax and immunosuppressant agents such as FK-506, rapamycin, cyclosporine, azathioprine, and methotrexate.

EXAMPLES

Example 1

General Synthetic Procedure I

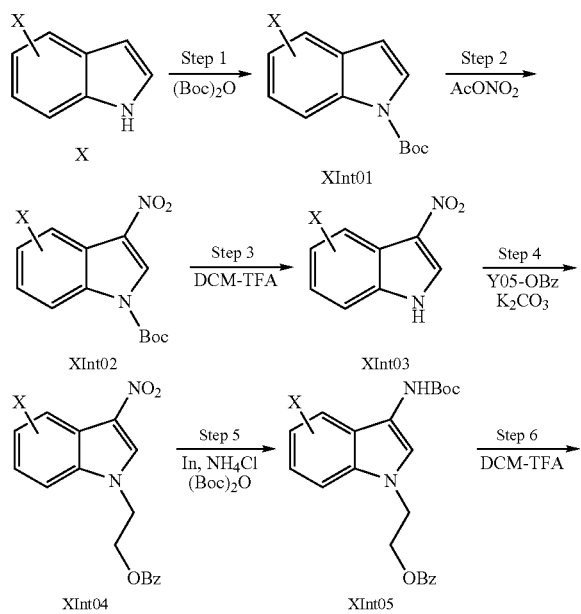

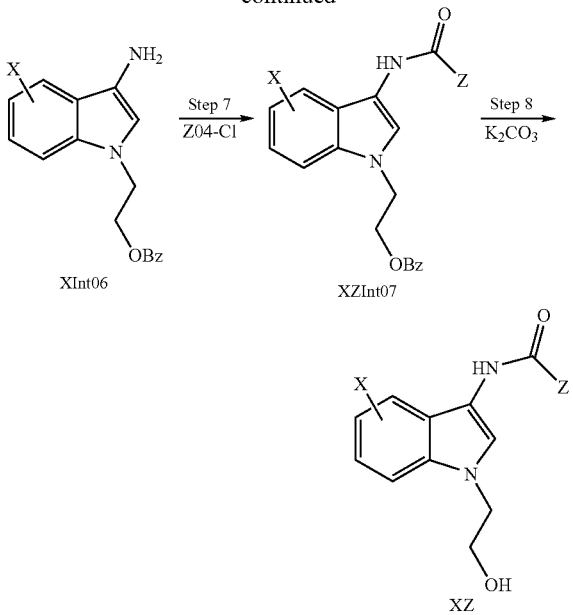

General Procedure for Preparation of XInt01:

To solution of the indole derivative X (1 eq) in TEA and DMAP in DCM at room temperature was added (Boc)$_2$O and the resultant reaction mixture was stirred at room temperature. After 1 hour, the reaction mixture was diluted with water and extracted 3 times with DCM. The combined DCM layers were washed with 1N HCl solution, dried over Na$_2$SO$_4$, and concentrated under reduced pressure to afford XInt01 as a liquid.

General Procedure for Preparation of XInt02:

To a stirring solution of XInt01 in Ac$_2$O at −78° C. was added an ice-cold solution of fuming HNO$_3$ in Ac$_2$O over a period of 15 minutes. The reaction mixture was slowly warmed to room temperature and stirred further. After 16 hours, it was diluted with ice water and extracted 3 times with EtOAc. The combined EtOAc layers were washed with brine, dried over Na$_2$SO$_4$ and concentrated under reduced pressure. Purification by flash chromatography (SiO$_2$, 100-200 mesh, 1% EtOAc in Petrolium ether) afforded XInt02 as a liquid.

General Procedure for Preparation of XInt03:

To a stirring solution of XInt02 in DCM was added TFA at 0° C. and the resultant reaction mixture was slowly warmed to room temperature and stirred further. After 2 hours, the reaction mixture was concentrated under reduced pressure to afford XInt03.

General Procedure for Preparation of XInt04:

To a stirring solution of XInt03 in dry DMF were added 2-chloroethyl benzoate (Y05-OBz) and K$_2$CO$_3$ and the resultant reaction mixture was heated to 60° C. After 16 hours, the reaction mixture was diluted with ice water and extracted 3 times with DCM. The combined DCM layers were dried over Na$_2$SO$_4$ and concentrated under reduced pressure. Purification by trituration afforded XInt04 as a solid.

General Procedure for Preparation of XInt05:

To a stirring solution of XInt04 in MeOH were added indium, (Boc)$_2$O and NH$_4$Cl. The reaction mixture was heated to reflux. After 30 minutes, it was filtered and the filtrate was concentrated under reduced pressure. The obtained residue was diluted with water and extracted 3 times with EtOAc. The combined EtOAc layers were washed with brine, dried over $Na_2SO_4$ and concentrated under reduced pressure. Purification by flash chromatography ($SiO_2$, 100-200 mesh, 5% EtOAc in Pet. ether) afforded XInt05 as a solid.

General Procedure for Preparation of XInt06:

To a stirring solution of XInt05 in DCM was added TFA at 0° C. and the resultant reaction mixture was slowly warmed to room temperature. After 2 hours, the reaction mixture was concentrated under reduced pressure to afford XInt06.

General Procedure for Preparation of XZInt07:

To a stirring solution of XInt06 in THF (3.0 mL) were added TFA (296 mg, 2.93 mmol) and an acid chloride Z (e.g. cyclohexyl acetic acid, cycloheptyl acetic acid, cyclohexyl propionic acid, or cycloheptyl propionic acid) at 0° C. and the resultant reaction mixture was slowly warmed to room temperature. After 30 minutes, the reaction mixture was diluted with water and extracted 3 times with EtOAc. The combined EtOAc layers were washed with brine, dried over $Na_2SO_4$ and concentrated under reduced pressure. Purification by trituration afforded XZInt07 as a solid.

General Procedure for Preparation of XZ:

To a stirring solution of XZInt07 in MeOH was added $K_2CO_3$ and the resultant reaction mixture was stirred at room temperature. After 30 minutes, the reaction mixture was filtered and the filerate was concentrated under reduced pressure. Purification of the residue by flash chromatography ($SiO_2$, 100-200 mesh, 50% EtOAc in Petroleum ether) afforded XZ as a solid.

Example 2

N-(4-chloro-1-(2-hydroxyethyl)-1H-indol-3-yl)-2-cycloheptylacetamide

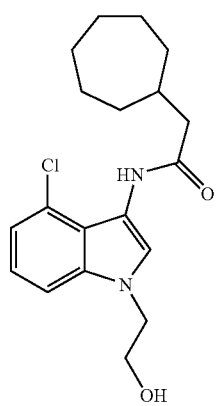

Synthesised according to the procedure disclosed in Example 1 where X is 4-chloro indole, Z is cycloheptyl acetyl chloride. Formula: $C_{19}H_{25}ClN_2O_2$; Molecular Weight: 348.9; Mass/charge ratio: 348.2 (100.0%), 350.2 (34.6%), 349.2 (21.7%), 351.2 (7.2%); Elemental analysis: C, 65.41; H, 7.22; Cl, 10.16; N, 8.03; O, 9.17.

Example 3

N-(4-bromo-1-(2-hydroxyethyl)-1H-indol-3-yl)-2-cycloheptylacetamide

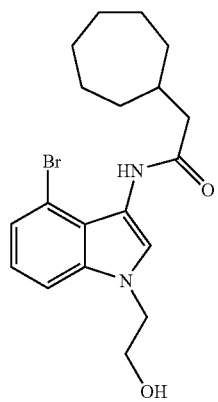

Synthesised according to the procedure disclosed in Example 1 where X is 4-bromo indole, Z is cycloheptyl acetyl chloride. Formula: $C_{19}H_{25}BrN_2O_2$; Molecular Weight: 393.3; Mass/charge ratio: 392.1 (100.0%), 394.1 (99.9%), 393.1 (21.7%), 395.1 (21.3%), 396.1 (2.6%); Elemental analysis: C, 58.02; H, 6.41; Br, 20.32; N, 7.12; O, 8.14.

Example 4

N-(4-chloro-1-(2-hydroxyethyl)-1H-indol-3-yl)-2-cyclohexylacetamide

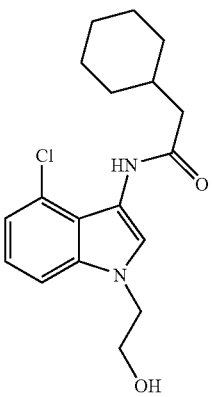

Synthesised according to the procedure disclosed in Example 1 where X is 4-chloro indole, Z is cyclohexyl acetyl chloride. Formula: $C_{18}H_{23}ClN_2O_2$; Molecular Weight: 334.8; Mass/charge ratio: 334.1 (100.0%), 336.1 (32.5%), 335.1 (20.3%), 337.1 (6.6%), 336.2 (1.9%); Elemental analysis: C, 64.57; H, 6.92; Cl, 10.59; N, 8.37; O, 9.56.

Example 5

N-(4-bromo-1-(2-hydroxyethyl)-1H-indol-3-yl)-2-cyclohexylacetamide

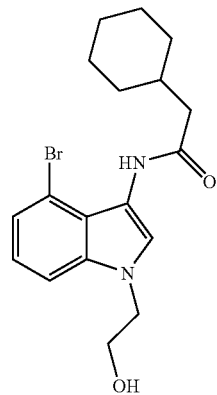

Synthesised according to the procedure disclosed in Example 1 where X is 4-bromo indole, Z is cyclohexyl acetyl chloride. Formula: $C_{18}H_{23}BrN_2O_2$; Molecular Weight: 379.3; Mass/charge ratio: 378.1 (100.0%), 380.1 (99.7%), 379.1 (20.5%), 381.1 (20.2%), 382.1 (2.4%); Elemental analysis: C, 57.00; H, 6.11; Br, 21.07; N, 7.39; O, 8.44.

Example 6

N-(4-chloro-1-(2-hydroxypropyl)-1H-indol-3-yl)-2-cycloheptylacetamide

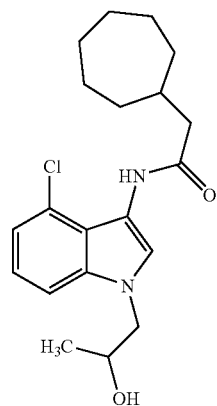

Synthesised according to the procedure disclosed in Example 20 where X is 4-chloro indole, Z is cycloheptyl acetyl chloride. Formula: $C_{20}H_{27}ClN_2O_2$; Molecular Weight: 362.9; Mass/charge ratio: 362.2 (100.0%), 364.2 (34.8%), 363.2 (22.8%), 365.2 (7.5%); Elemental analysis: C, 66.19; H, 7.50; Cl, 9.77; N, 7.72; O, 8.82.

Example 7

N-(4-bromo-1-(2-hydroxypropyl)-1H-indol-3-yl)-2-cycloheptylacetamide

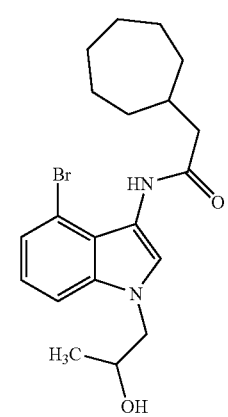

Synthesised according to the procedure disclosed in Example 20 where X is 4-bromo indole, Z is cycloheptyl acetyl chloride. Formula: $C_{20}H_{27}BrN_2O_2$; Molecular Weight: 407.3; Mass/charge ratio: 408.1 (100.0%), 406.1 (99.8%), 407.1 (22.7%), 409.1 (22.4%), 410.1 (2.8%); Elemental analysis: C, 58.97; H, 6.68; Br, 19.62; N, 6.88; O, 7.86.

Example 8

N-(4-chloro-1-(2-hydroxyethyl)-1H-indol-3-yl)-3-cyclohexylpropanamide

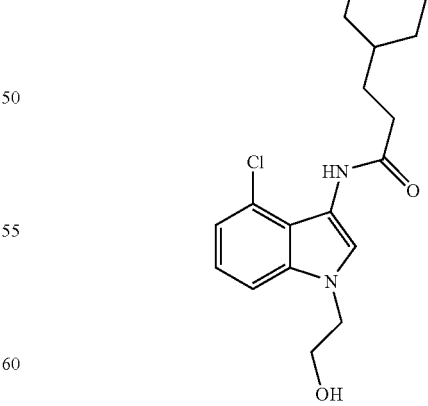

Synthesised according to the procedure disclosed in Example 1 where X is 4-chloro indole, Z is cyclohexylproprionyl chloride. Formula: $C_{19}H_{25}ClN_2O_2$; Molecular Weight: 348.9; Mass/charge ratio: 348.2 (100.0%), 350.2 (34.6%), 349.2 (21.7%), 351.2 (7.2%); Elemental analysis: C, 65.41; H, 7.22; Cl, 10.16; N, 8.03; O, 9.17.

Example 9

N-(4-bromo-1-(2-hydroxyethyl)-1H-indol-3-yl)-3-cyclohexylpropanamide

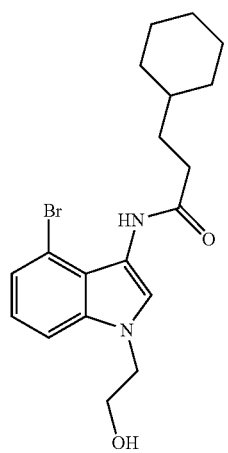

Synthesised according to the procedure disclosed in Example 1 where X is 4-bromo indole, Z is cyclohexylproprionyl chloride. Formula: $C_{19}H_{25}BrN_2O_2$; Molecular Weight: 393.3; Mass/charge ratio: 392.1 (100.0%), 394.1 (99.9%), 393.1 (21.7%), 395.1 (21.3%), 396.1 (2.6%); Elemental analysis: C, 58.02; H, 6.41; Br, 20.32; N, 7.12; O, 8.14.

Example 10

N-(4-chloro-1-(2-hydroxyethyl)-1H-indol-3-yl)-3-cycloheptylpropanamide

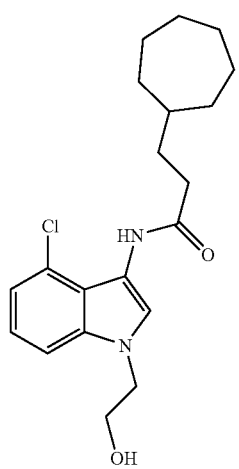

Synthesised according to the procedure disclosed in Example 1 where X is 4-chloro indole, Z is cycloheptylproprionyl chloride. Formula: $C_{20}H_{27}ClN_2O_2$; Molecular Weight: 362.9; Mass/charge ratio: 362.2 (100.0%), 364.2 (34.8%), 363.2 (22.8%), 365.2 (7.5%); Elemental analysis: C, 66.19; H, 7.50; Cl, 9.77; N, 7.72; O, 8.82.

Example 11

N-(4-bromo-1-(2-hydroxyethyl)-1H-indol-3-yl)-3-cycloheptylpropanamide

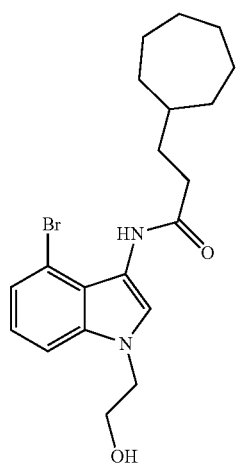

Synthesised according to the procedure disclosed in Example 1 where X is 4-bromo indole, Z is cycloheptylproprionyl chloride. Formula: $C_{20}H_{27}BrN_2O_2$; Molecular Weight: 407.3; Mass/charge ratio: 408.1 (100.0%), 406.1 (99.8%), 407.1 (22.7%), 409.1 (22.4%), 410.1 (2.8%); Elemental analysis: C, 58.97; H, 6.68; Br, 19.62; N, 6.88; O, 7.86.

Example 12

N-(4-chloro-1-(2-hydroxyethyl)-1H-pyrrolo[2,3-b]pyridin-3-yl)-2-cyclohexylacetamide

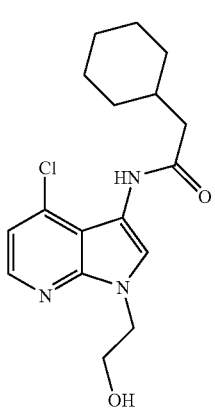

Synthesised according to the procedure disclosed in Example 1 where X is 4-chloro-1H-pyrrolo[2,3-b]pyridine, Z is cyclohexyl acetyl chloride. Formula: $C_{17}H_{22}ClN_3O_2$; Molecular Weight: 335.8; Mass/charge ratio: 335.1

(100.0%), 337.1 (34.2%), 336.1 (19.8%), 338.1 (6.4%); Elemental analysis: C, 60.80; H, 6.60; Cl, 10.56; N, 12.51; O, 9.53.

Example 13

N-(4-bromo-1-(2-hydroxyethyl)-1H-pyrrolo[2,3-b]pyridin-3-yl)-2-cyclohexylacetamide

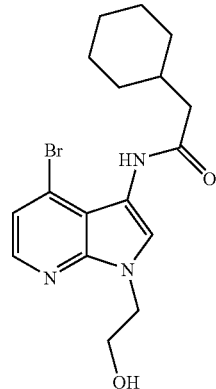

Synthesised according to the procedure disclosed in Example 1 where X is 4-bromo-1H-pyrrolo[2,3-b]pyridine, Z is cyclohexyl acetyl chloride. Formula: $C_{17}H_{22}BrN_3O_2$; Molecular Weight: 380.3; Mass/charge ratio: 379.1 (100.0%), 381.1 (99.6%), 380.1 (19.8%), 382.1 (19.5%), 383.1 (2.2%); Elemental analysis: C, 53.69; H, 5.83; Br, 21.01; N, 11.05; O, 8.41.

Example 14

N-(4-chloro-1-(2-hydroxyethyl)-1H-pyrrolo[2,3-b]pyridin-3-yl)-2-cycloheptylacetamide

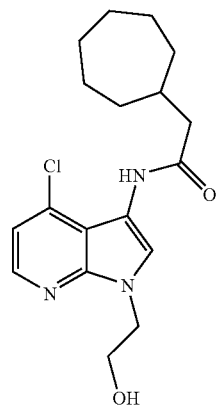

Synthesised according to the procedure disclosed in Example 1 where X is 4-chloro-1H-pyrrolo[2,3-b]pyridine, Z is cycloheptyl acetyl chloride. Formula: $C_{18}H_{24}ClN_3O_2$; Molecular Weight: 349.9; Mass/charge ratio 349.2 (100.0%), 351.2 (34.5%), 350.2 (20.9%), 352.2 (6.6%); Elemental analysis: C, 61.79; H, 6.91; Cl, 10.13; N, 12.01; O, 9.15.

Example 15

N-(4-bromo-1-(2-hydroxyethyl)-1H-pyrrolo[2,3-b]pyridin-3-yl)-2-cycloheptylacetamide

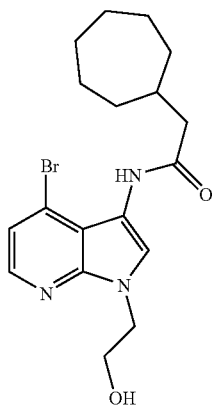

Synthesised according to the procedure disclosed in Example 1 where X is 4-bromo-1H-pyrrolo[2,3-b]pyridine, Z is cycloheptyl acetyl chloride. Formula: $C_{18}H_{24}BrN_3O_2$; Molecular Weight: 394.3; Mass/charge ratio: 393.1 (100.0%), 395.1 (99.8%), 394.1 (20.9%), 396.1 (20.6%), 397.1 (2.4%); Elemental analysis: C, 54.83; H, 6.13; Br, 20.26; N, 10.66; O, 8.12.

Example 16

N-(4-chloro-1-(2-hydroxypropyl)-1H-pyrrolo[2,3-b]pyridin-3-yl)-2-cycloheptylacetamide

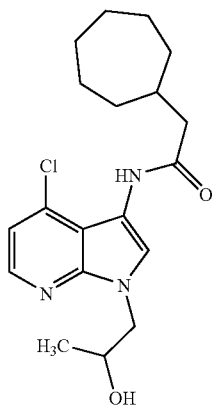

Synthesised according to the procedure disclosed in Example 20 where X is 4-chloro-1H-pyrrolo[2,3-b]pyridine, Z is cycloheptyl acetyl chloride. Formula: $C_{19}H_{26}ClN_3O_2$; Molecular Weight: 363.9; Mass/charge ratio: 363.2

(100.0%), 365.2 (34.7%), 364.2 (22.0%), 366.2 (7.3%); Elemental analysis: C, 62.71; H, 7.20; Cl, 9.74; N, 11.55; O, 8.79.

Example 17

N-(4-bromo-1-(2-hydroxypropyl)-1H-pyrrolo[2,3-b]pyridin-3-yl)-2-cycloheptylacetamide

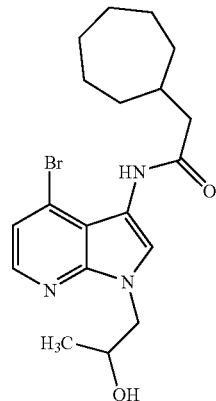

Synthesised according to the procedure disclosed in Example 20 where X is 4-bromo-1H-pyrrolo[2,3-b]pyridine, Z is cycloheptyl acetyl chloride. Formula: $C_{19}H_{26}BrN_3O_2$; Molecular Weight: 408.3; Mass/charge ratio: 409.1 (100.0%), 407.1 (100.0%), 408.1 (22.0%), 410.1 (21.7%), 411.1 (2.7%); Elemental analysis: C, 55.89; H, 6.42; Br, 19.57; N, 10.29; O, 7.84.

Example 18

N-(4-chloro-1-(2-hydroxyethyl)-1H-pyrrolo[2,3-b]pyridin-3-yl)-3-cyclohexylpropanamide

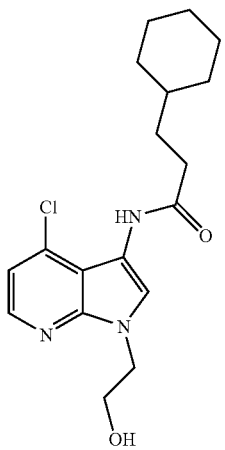

Synthesised according to the procedure disclosed in Example 1 where X is 4-chloro-1H-pyrrolo[2,3-b]pyridine, Z is cyclohexylproprionyl chloride. Formula: $C_{18}H_{24}ClN_3O_2$; Molecular Weight: 349.9; Mass/charge ratio: 349.2 (100.0%), 351.2 (34.5%), 350.2 (20.9%), 352.2 (6.6%); Elemental analysis: C, 61.79; H, 6.91; Cl, 10.13; N, 12.01; O, 9.15.

Example 19

N-(4-bromo-1-(2-hydroxyethyl)-1H-pyrrolo[2,3-b]pyridin-3-yl)-3-cyclohexylpropanamide

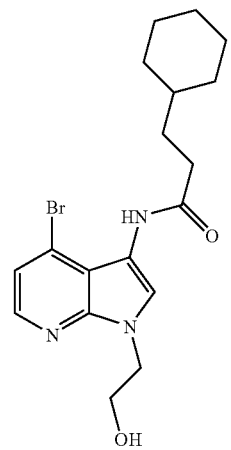

Synthesised according to the procedure disclosed in Example 1 where X is 4-bromo-1H-pyrrolo[2,3-b]pyridine, Z is cyclohexylpropionyl chloride. Formula: $C_{18}H_{24}BrN_3O_2$; Molecular Weight: 394.3; Mass/charge ratio: 393.1 (100.0%), 395.1 (99.8%), 394.1 (20.9%), 396.1 (20.6%), 397.1 (2.4%); Elemental analysis: C, 54.83; H, 6.13; Br, 20.26; N, 10.66; O, 8.12.

Further preferred examples include the following compounds:

Example 20

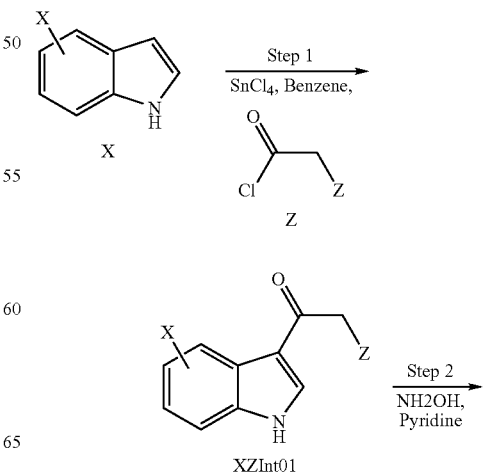

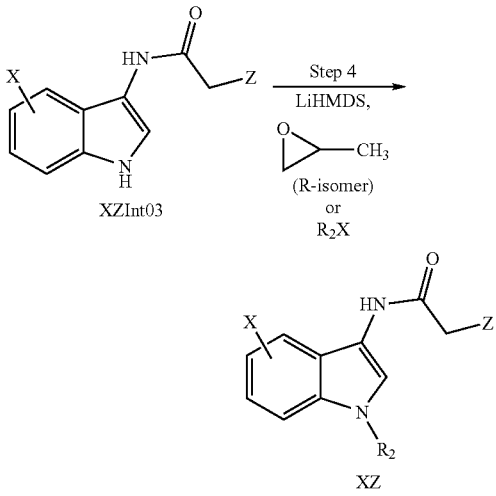

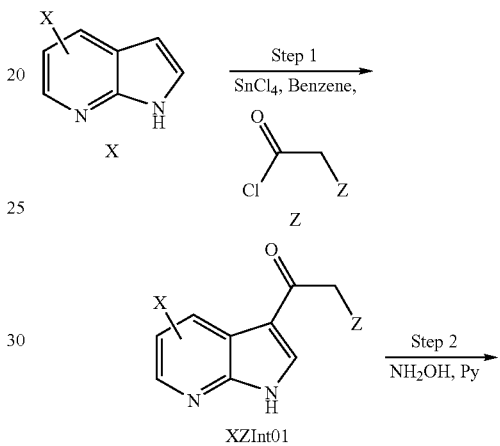

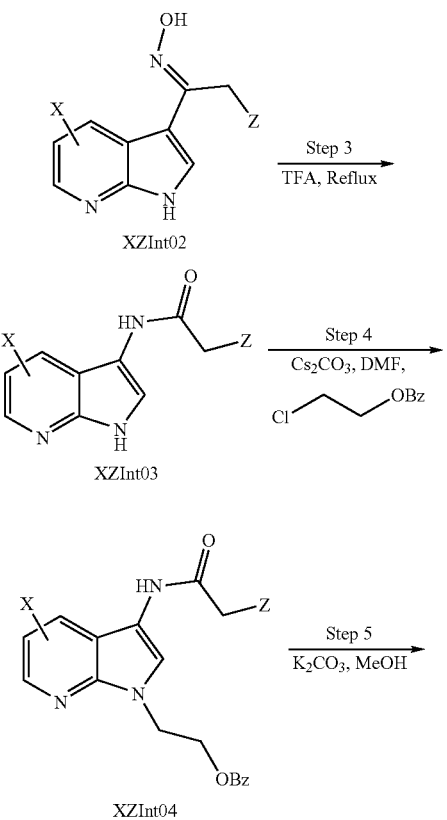

General Procedure for the Preparation of XZInt01

To a solution of an indole derivative X (6.6 mmol) in dry benzene (10 ml) was added an acid chloride Z (e.g. 2-cyclohexylacetyl chloride, 2-cycloheptylacetyl chloride, 2-cyclohexylpropionyl chloride, 2-cycloheptylpropionyl chloride) (13 mmol) in dry benzene (10 mL) at 0° C. A solution of $SnCl_4$ (26.49 mM) in dry benzene (15 mL) was added dropwise at 0° C. The reaction mixture was allowed to warm to room temperature and maintained for 3 hr. The mixture was poured into 5% aq HCl (50 mL) and ethyl acetate (100 mL) and stirred for 10 min. The organic layer was separated and washed with water (50 mL), sat $NaHCO_3$ solution (50 mL), brine (50 mL), dried over anhydrous sodium sulfate and concentrated. The crude material was purified by silica gel column using ethyl acetate and chloroform to obtain the pure XZInt01.

General Procedure for the Preparation of XZInt02

To a stirred solution of XZInt01 (2.25 mmol) in methanol (10 ml) were added $NH_2OH \cdot HCl$ (4.49 mM), and pyridine (6.74 mM) at room temperature. Then the mixture was refluxed for 2 hr. Methanol was distilled off and the residue obtained was dissolved in ethyl acetate (75 mL), washed with water (50 mL), brine (50 mL), dried over anhydrous sodium sulfate and concentrated. The crude product was purified over silica gel column using ethyl acetate and hexane to yield XZInt02.

General Procedure for the Preparation of XZInt03

XZInt02 (1.8 mmol) in TFA (15 mL) was refluxed for 5 hr. Then the reaction mixture concentrated to obtain a residue. This residue was dissolved in Ethyl acetate (100 mL) and washed with water (50 mL), saturated sodium bicarbonate solution (50 mL), water (50 mL) and brine (50 mL). The organic layer was dried over anhydrous sodium sulfate and concentrated. The crude product was purified over silica gel column using ethyl acetate and hexane to yield XZInt03.

General Procedure for the Preparation of XZ

The mixture of XZInt03 (0.33 mmol), (R)-2-propylene oxide or alkyliodide (3.3 mmol) and $Cs_2CO_3$ (1.64 mmol) in dry DMF (2 mL) was maintained at 120° C. for 20 minutes in a microwave. Then the reaction mixture was poured into water and extracted with ethyl acetate (100 mL). The organic layer was washed with water (50 mL), brine (50 mL), dried over anhydrous sodium sulfate and concentrated. The crude product was purified over silica gel column to yield XZ.

Example 21

General Synthetic Procedure III

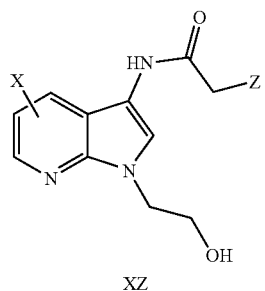

XZ

General Procedure for the preparation of XZInt01

To a solution of azaindole derivative X (6.5 mmol) in dry benzene was added to an acid chloride Z (e.g. 2-cyclohexylacetyl chloride, 2-cycloheptylacetyl chloride, 2-cyclohexylpropionyl chloride, 2-cycloheptylpropionyl chloride) (13 mmol) at 0° C. and stirred for 10 min. To this $SnCl_4$ (26.2 mmol) was added drop-wise at 0° C. The reaction mixture was slowly allowed to warm to room temperature and stirred for 3 hr. The reaction mixture was poured into 2N HCl (50 mL) and extracted with ethyl acetate (100 mL). The organic layer was washed with water (50 mL), sat NaHCO3 solution (50 m), brine (50 mL) and dried over anhydrous sodium sulfate to yield XZInt01.

General Procedure for the preparation of XZInt02

To a stirred solution of XZInt01 (2.8 mmol) in methanol (16 mL) were added $NH_2OH.HCl$ (5.75 mmol) and pyridine (8.6 mmol) at room temperature. The reaction mixture was heated to reflux for 2 hr, evaporated and the residue was diluted with water (75 mL) and extracted with ethyl acetate (2×50 mL). The combined organic layer was washed with brine (50 mL), dried over anhydrous sodium sulfate and concentrated. The crude product was purified over silica gel column using ethyl acetate and hexane to yield XZInt02.

General Procedure for the preparation of XZInt03

XZInt02 (1.7 mmol) in TFA (15 ml) was refluxed for 5 hours. The reaction mixture was concentrated and the residue was diluted with water (50 mL) and extracted with ethyl acetate (2×50 mL). The combined organic layer was washed with sat $NaHCO_3$ solution (50 mL), brine (50 mL), dried over anhydrous sodium sulfate and concentrated The crude product was purified over silica gel column using ethyl acetate and hexane to yield XZInt03.

General Procedure for the Preparation of XZInt04

To a stirred solution of XZInt03 (1.2 mmol) in DMF was added $Cs_2CO_3$ (3.6 mmol) at room temperature and stirred for 15 min. Chloroethyl benzoate (1.8 mmol) was added and the mixture was heated to 80° C. and stirred for 16 hrs. The reaction mixture was poured into ice cold water and extracted with ethyl acetate (2×50 mL). The combined organic layer was washed with brine (50 mL), dried over anhydrous sodium sulfate and concentrated. The crude product was purified over silica gel column using ethyl acetate and hexane to yield XZInt04

General Procedure for the Preparation of XZ

To a solution of XZInt04 (0.3 mmol) in methanol (10 mL) was added $K_2CO_3$ (1.0 mmol) at room temperature and stirred for 1 hr. The reaction mixture was concentrated and the residue was diluted with water (10 mL) and extracted with ethyl acetate (2×25 mL). The ethyl acetate layer was washed with brine (20 mL), dried over anhydrous sodium sulfate and concentrated. The crude product was triturated with diethyl ether to yield XZ.

Example 22

General Synthetic Procedure VI

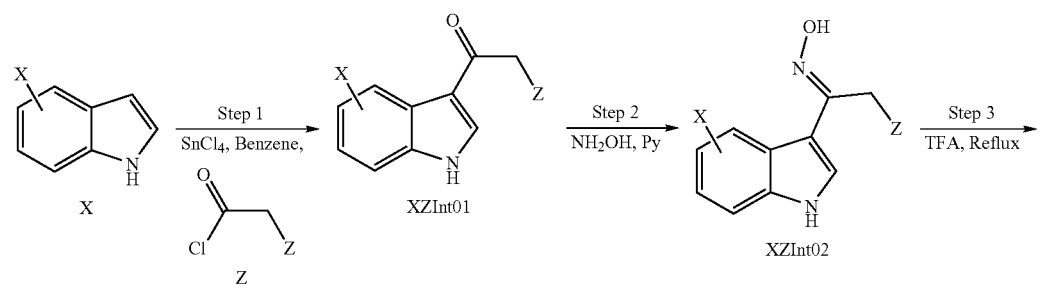

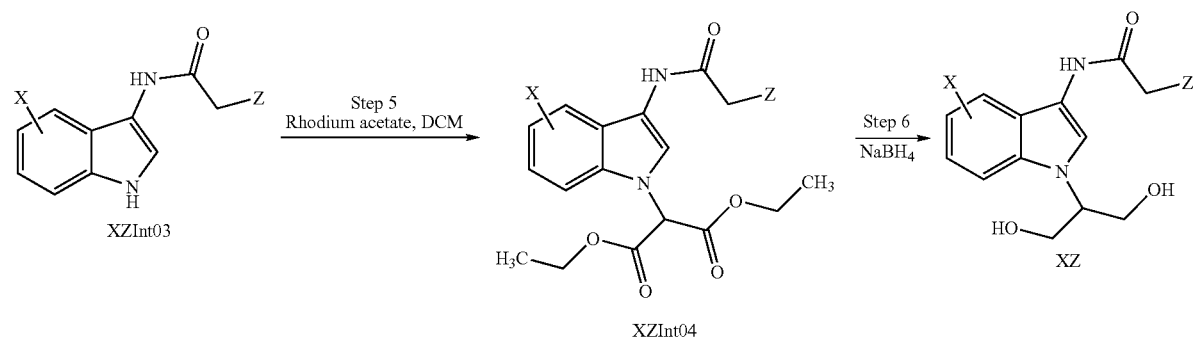

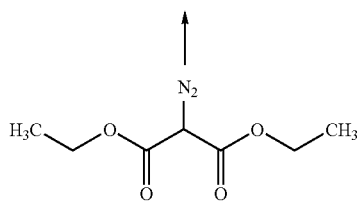

Step 4 | PTSA, NaN₃, TEA

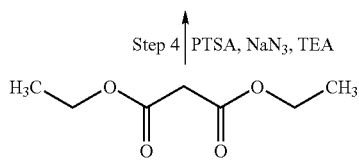

Preparation of diethyl 2-(4-chloro-3(-2-cycloheptylacetamido)-indol-1-yl)malonate (Step 4)

To a solution of sodium azide (4.2 g, 64.6 mmol) in 70% aqueous ethanol (150 mL) was added p-toluenesulphonyl chloride (11.8 g, 65.5 mmol) at room temperature and stirred for 1 h at room temperature. Diethyl malonate (10 g, 62.5 mm) and triethylamine (6.3 g, 65.5 mm) were added and the reaction mixture was stirred at room temperature for 1.5 hour. The reaction mixture was poured into water and extracted with hexane (2×50 mL). The combined organic layer was once washed with brine solution (50 mL), dried over anhydrous sodium sulfate and concentrated under reduced pressure to obtain diethyl 2-(4-chloro-3(-2-cycloheptylacetamide)-indol-1-yl)-malonate as yellow oil (9 g, 77.5%)

General Procedure for the Preparation of XZInt04

To a solution of XZInt03 (1.6 mmol; see example 20) in DCM (5 ml) was added Rhodium acetate (0.32 mmol) and diethyl 2-(4-chloro-3(-2-cycloheptylacetamido)-indol-1-yl)-malonate (4.0 mmol) and the reaction mixture was stirred at room temperature for 12 hours. Water (50 ml) was added followed by extraction with ethyl acetate (50 ml×3). The combined organic layer was once washed with brine solution and dried over anhydrous sodium sulfate and concentrated under reduced pressure. The crude material was purified by flash column chromatography using 100-200 mesh size silica gel and the product XZInt04 was eluted with 7% ethyl acetate/chloroform.

General Procedure for the Preparation of XZ

To a stirred solution of XZInt04 (0.54 mmol) in methanol was added sodium borohydride (2.6 mmol) under nitrogen atmosphere at 0° C. and the reaction mixture was allowed to warm to room temperature and was stirred for 2 hours. The reaction mixture was concentrated under reduced pressure. The residue was dissolved in water (25 mL) and extracted with ethyl acetate (2×25 mL). The combined organic layer was washed with brine (20 mL) and dried over anhydrous sodium sulphate and concentrated. Purification by flash column chromatography using 100-200 mesh size silica gel (3% methanol/chloroform) yielded XZ.

Example 23

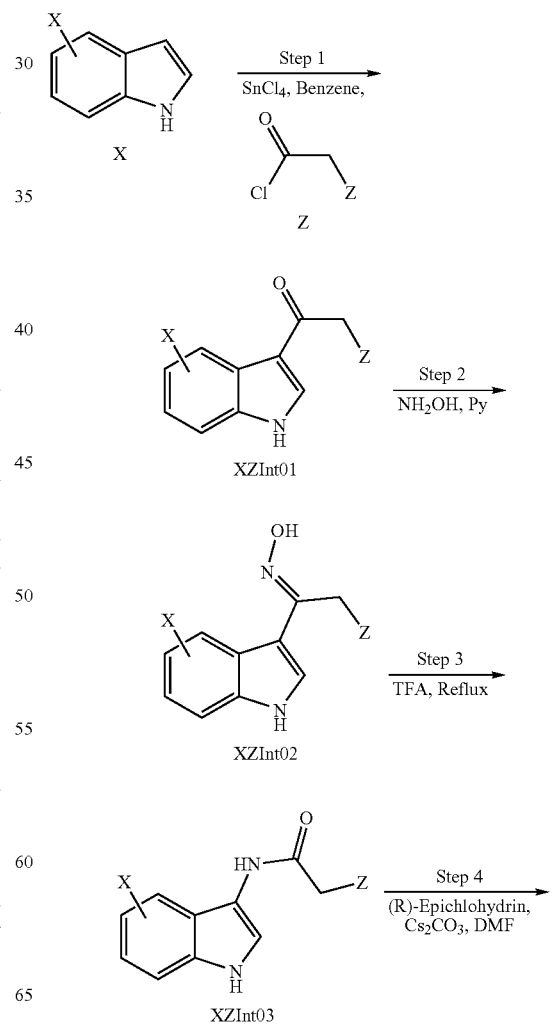

-continued

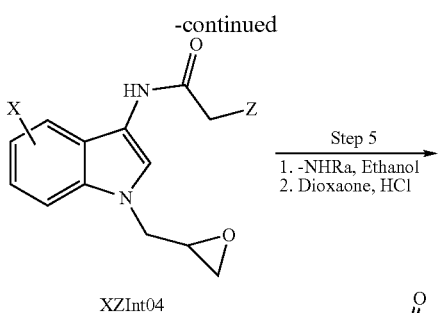

XZInt04

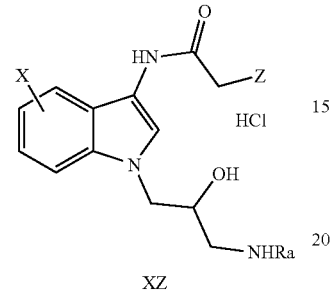

XZ

General Procedure for the Preparation of XZInt04

To a solution of XZInt03 (1.9 mmol; see example 20) in DMF (6 ml) was added $K_2CO_3$ (5.9 mmol) at room temperature and the reaction mixture was stirred for 10 min. R-(−) Epichlorohydrin (5.9 mmol) was added under nitrogen atmosphere and the reaction mixture was heated at 85° for 12 hours. Then reaction mixture was poured into ice water and extracted with ethyl acetate (50 ml×3). The combined organic layer was once washed with brine solution (25 ml) and dried over anhydrous sodium sulfate and concentrated under reduced pressure. The crude product was purified over silica gel column (100-200 mesh size) using ethyl acetate/hexane as solvent to yield XZInt04.

General Procedure for the Preparation of XZ

To a solution of XZInt04 (0.55 mmol) in ethanol (5 ml) was added aqueous ammonia or alkylamine (10 ml) and the reaction mixture was refluxed for 1 hour. The reaction mixture was concentrated under reduced pressure and co-distilled with ethanol and triturated with pentane and diethyl ether to yield the crude product as a solid followed by HPLC purification. Treatment with dioxane-HCl yielded the HCl salt of XZ.

Example 24

N-(4-chloro-1-(2-hydroxypropyl)-1H-indol-3-yl)-2-cyclohexylacetamide

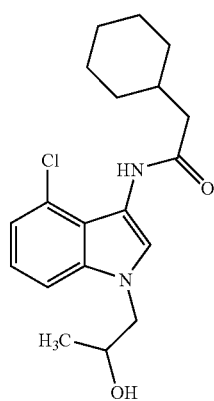

Synthesised according to the procedure disclosed in Example 20 where X is 4-chloro indole, Z is 2-cyclohexylacetyl chloride. Formula: $C_{19}H_{25}ClN_2O_2$; Molecular Weight: 348.9; Mass/charge ratio: 348.2 (100.0%), 350.2 (34.6%), 349.2 (21.7%), 351.2 (7.2%); Elemental analysis: C, 65.41; H, 7.22; Cl, 10.16; N, 8.03; O, 9.17.

Example 25

N-(4-bromo-1-(2-hydroxypropyl)-1H-indol-3-yl)-2-cyclohexylacetamide

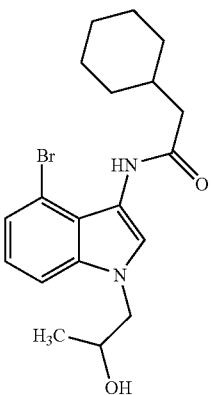

Synthesised according to the procedure disclosed in Example 20 where X is 4-bromo indole, Z is 2-cyclohexylacetyl chloride. Formula: $C_{19}H_{25}BrN_2O_2$; Molecular Weight: 393.3; Mass/charge ratio: 392.1 (100.0%), 394.1 (99.9%), 393.1 (21.7%), 395.1 (21.3%), 396.1 (2.6%); Elemental analysis: C, 58.02; H, 6.41; Br, 20.32; N, 7.12; O, 8.14.

Example 26

2-(bicyclo[2.2.2]octan-1-yl)-N-(4-chloro-1-(2-hydroxypropyl)-1H-indol-3-yl)acetamide

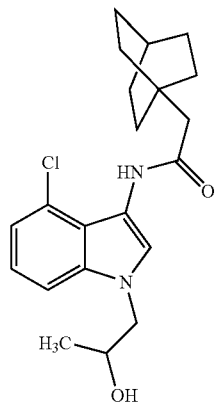

Synthesised according to the procedure disclosed in Example 20 where X is 4-chloro indole, Z is bicyclo[2.2.2] octan-1-yl acetyl chloride. Formula: $C_{21}H_{27}ClN_2O_2$; Molecular Weight: 374.9; Mass/charge ratio: 374.2

(100.0%), 376.2 (35.1%), 375.2 (23.8%), 377.2 (7.9%), 378.2 (1.0%); Elemental analysis: C, 67.28; H, 7.26; Cl, 9.46; N, 7.47; O, 8.54.

Example 27

2-(bicyclo[2.2.2]octan-1-yl)-N-(4-bromo-1-(2-hydroxypropyl)-1H-indol-3-yl)acetamide

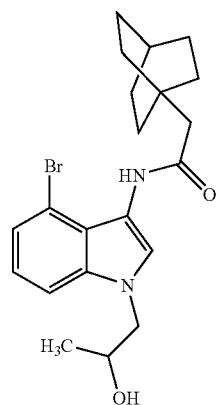

Synthesised according to the procedure disclosed in Example 20 where X is 4-bromo indole, Z is bicyclo[2.2.2]octan-1-yl acetyl chloride. Formula: $C_{21}H_{27}BrN_2O_2$; Molecular Weight: 419.4; Mass/charge ratio: 420.1 (100.0%), 418.1 (99.6%), 419.1 (23.7%), 421.1 (23.4%), 422.1 (3.1%); Elemental analysis: C, 60.15; H, 6.49; Br, 19.05; N, 6.68; O, 7.63.

Example 28

N-(4-chloro-1-(2-hydroxypropyl)-1H-indol-3-yl)-3-cyclohexylpropanamide

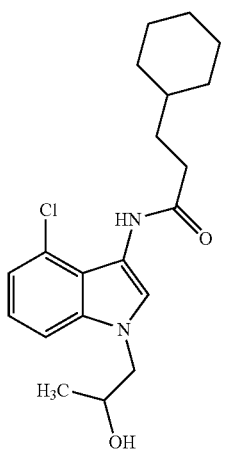

Synthesised according to the procedure disclosed in Example 20 where X is 4-chloro indole, Z is 2-cyclohexylpropionyl chloride. Formula: $C_{20}H_{27}ClN_2O_2$; Molecular Weight: 362.9; Mass/charge ratio: 362.2 (100.0%), 364.2 (34.8%), 363.2 (22.8%), 365.2 (7.5%); Elemental analysis: C, 66.19; H, 7.50; Cl, 9.77; N, 7.72; O, 8.82.

Example 29

N-(4-bromo-1-(2-hydroxypropyl)-1H-indol-3-yl)-3-cyclohexylpropanamide

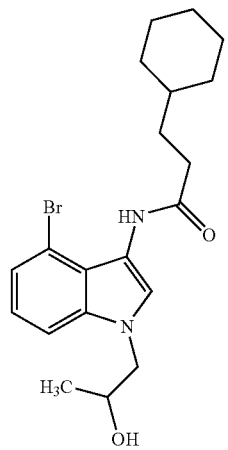

Synthesised according to the procedure disclosed in Example 20 where X is 4-bromo indole, Z is 2-cyclohexylpropionyl chloride. Formula: $C_{20}H_{27}BrN_2O_2$; Molecular Weight: 407.3; Mass/charge ratio: 408.1 (100.0%), 406.1 (99.8%), 407.1 (22.7%), 409.1 (22.4%), 410.1 (2.8%); Elemental analysis: C, 58.97; H, 6.68; Br, 19.62; N, 6.88; O, 7.86.

Example 30

N-(4-chloro-1-(2-hydroxypropyl)-1H-indol-3-yl)-3-cycloheptylpropanamide

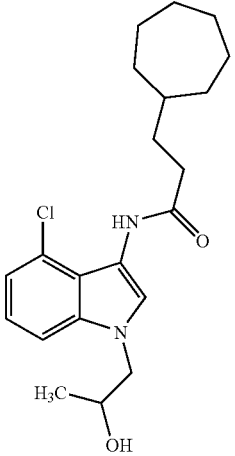

Synthesised according to the procedure disclosed in Example 20 where X is 4-chloro indole, Z is 2-cycloheptylpropionyl chloride. Formula: $C_{21}H_{29}ClN_2O_2$; Molecular Weight: 376.9; Mass/charge ratio: 376.2 (100.0%), 378.2

(35.1%), 377.2 (23.9%), 379.2 (7.9%), 380.2 (1.0%); Elemental analysis: C, 66.92; H, 7.76; Cl, 9.41; N, 7.43; O, 8.49.

Example 31

N-(4-bromo-1-(2-hydroxypropyl)-1H-indol-3-yl)-3-cycloheptylpropanamide

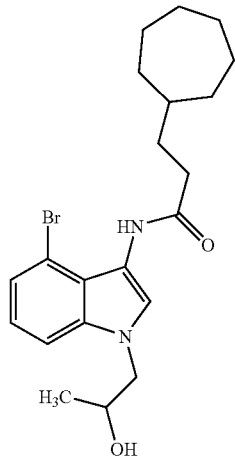

Synthesised according to the procedure disclosed in Example 20 where X is 4-bromo indole, Z is 2-cycloheptylpropionyl chloride. Formula: $C_{21}H_{29}BrN_2O_2$; Molecular Weight: 421.4; Mass/charge ratio: 422.1 (100.0%), 420.1 (99.7%), 421.1 (23.8%), 423.1 (23.2%), 424.1 (3.0%); Elemental analysis: C, 59.86; H, 6.94; Br, 18.96; N, 6.65; O, 7.59.

Example 32

N-(4-chloro-1-(1,3-dihydroxypropan-2-yl)-1H-indol-3-yl)-2-cyclohexylacetamide

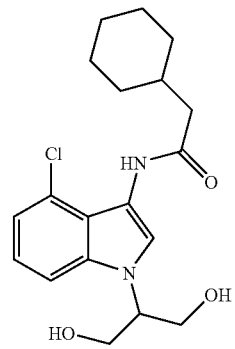

Synthesised according to the procedure disclosed in Example 22 where X is 4-chloro indole, Z is 2-cyclohexylacetyl chloride. Formula: $C_{19}H_{25}ClN_2O_3$; Molecular Weight: 364.9; Mass/charge ratio: 364.2 (100.0%), 366.2 (34.8%), 365.2 (21.7%), 367.2 (7.0%); Elemental analysis: C, 62.54; H, 6.91; Cl, 9.72; N, 7.68; O, 13.16.

Example 33

N-(4-bromo-1-(1,3-dihydroxypropan-2-yl)-1H-indol-3-yl)-2-cyclohexylacetamide

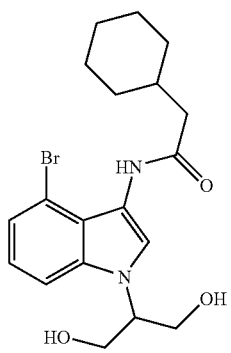

Synthesised according to the procedure disclosed in Example 22 where X is 4-bromo indole, Z is 2-cyclohexylacetyl chloride. Formula: $C_{19}H_{25}BrN_2O_3$; Molecular Weight: 409.3; Mass/charge ratio: 410.1 (100.0%), 408.1 (99.9%), 409.1 (21.7%), 411.1 (21.4%), 412.1 (2.8%); Elemental analysis C, 55.75; H, 6.16; Br, 19.52; N, 6.84; O, 11.73.

Example 34

N-(4-chloro-1-(1,3-dihydroxypropan-2-yl)-1H-indol-3-yl)-2-cycloheptylacetamide

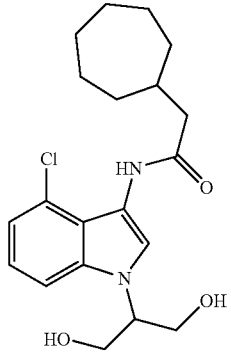

Synthesised according to the procedure disclosed in Example 22 where X is 4-chloro indole, Z is 2-cycloheptylacetyl chloride. Formula: $C_{20}H_{27}ClN_2O_3$; Molecular Weight: 378.9; Mass/charge ratio 378.2 (100.0%), 380.2

(35.1%), 379.2 (22.8%), 381.2 (7.6%), 382.2 (1.0%); Elemental analysis: C, 63.40; H, 7.18; Cl, 9.36; N, 7.39; O, 12.67.

Example 35

N-(4-bromo-1-(1,3-dihydroxypropan-2-yl)-1H-indol-3-O-2-cycloheptylacetamide

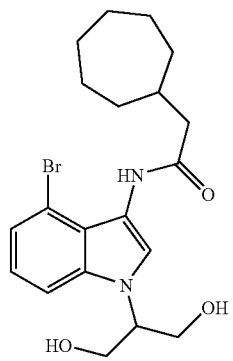

Synthesised according to the procedure disclosed in Example 22 where X is 4-bromo indole, Z is 2-cycloheptylacetyl chloride. Formula: $C_{20}H_{27}BrN_2O_3$; Molecular Weight 423.3; Mass/charge ratio: 424.1 (100.0%), 422.1 (99.6%), 423.1 (22.7%), 425.1 (22.4%), 426.1 (3.0%); Elemental analysis: C, 56.74; H, 6.43; Br, 18.87; N, 6.62; O, 11.34.

Example 36

2-(bicyclo[2.2.2]octan-1-yl)-N-(4-chloro-1-(1,3-dihydroxypropan-2-yl)-1H-indol-3-yl)acetamide

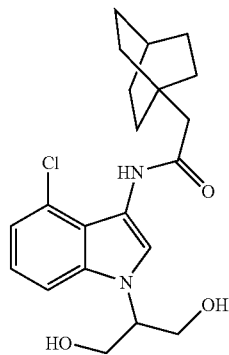

Synthesised according to the procedure disclosed in Example 22 where X is 4-chloro indole, Z is bicyclo[2.2.2]octan-1-yl acetyl chloride. Formula: $C_{21}H_{27}ClN_2O_3$; Molecular Weight: 390.9; Mass/charge ratio: 390.2 (100.0%), 392.2 (35.3%), 391.2 (23.9%), 393.2 (8.0%), 394.2 (1.1%); Elemental analysis: C, 64.52; H, 6.96; Cl, 9.07; N, 7.17; O, 12.28.

Example 37

2-(bicyclo[2.2.2]octan-1-yl)-N-(4-bromo-1-(1,3-dihydroxypropan-2-yl)-1H-indol-3-yl)acetamide

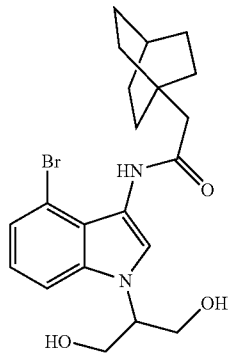

Synthesised according to the procedure disclosed in Example 22 where X is 4-bromo indole, Z is bicyclo[2.2.2]octan-1-yl acetyl chloride. Formula: $C_{21}H_{27}BrN_2O_3$; Molecular Weight: 435.4; Mass/charge ratio: 436.1 (100.0%), 434.1 (99.4%), 435.1 (23.7%), 437.1 (23.4%), 438.1 (3.3%); Elemental analysis: C, 57.94; H, 6.25; Br, 18.35; N, 6.43; O, 11.03.

Example 38

N-(4-chloro-1-(1,3-dihydroxypropan-2-yl)-1H-indol-3-yl)-3-cyclohexylpropanamide

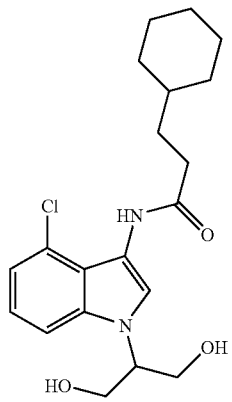

Synthesised according to the procedure disclosed in Example 22 where X is 4-chloro indole, Z is 2-cyclohexylpropionyl chloride. Formula: $C_{20}H_{27}ClN_2O_3$; Molecular Weight: 378.9; Mass/charge ratio: 378.2 (100.0%), 380.2

(35.1%), 379.2 (22.8%), 381.2 (7.6%), 382.2 (1.0%); Elemental analysis: C, 63.40; H, 7.18; Cl, 9.36; N, 7.39; O, 12.67.

Example 39

N-(4-bromo-1-(1,3-dihydroxypropan-2-yl)-1H-indol-3-yl)-3-cyclohexylpropanamide

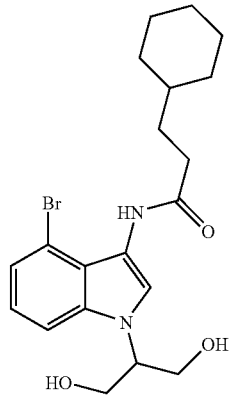

Synthesised according to the procedure disclosed in Example 22 where X is 4-bromo indole, Z is 2-cyclohexylpropionyl chloride. Formula: $C_{20}H_{27}BrN_2O_3$; Molecular Weight: 423.3; Mass/charge ratio: 424.1 (100.0%), 422.1 (99.6%), 423.1 (22.7%), 425.1 (22.4%), 426.1 (3.0%); Elemental analysis: C, 56.74; H, 6.43; Br, 18.87; N, 6.62; O, 11.34.

Example 40

N-(4-chloro-1-(1,3-dihydroxypropan-2-yl)-1H-indol-3-yl)-3-cycloheptylpropanamide

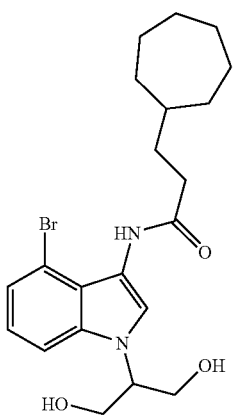

Synthesised according to the procedure disclosed in Example 22 where X is 4-chloro indole, Z is 2-cycloheptylpropionyl chloride. Formula: $C_{21}H_{29}ClN_2O_3$; Molecular Weight: 392.9; Mass/charge ratio: 392.2 (100.0%), 394.2

(35.3%), 393.2 (23.9%), 395.2 (8.0%), 396.2 (1.1%); Elemental analysis: C, 64.19; H, 7.44; Cl, 9.02; N, 7.13; O, 12.22.

Example 41

N-(4-bromo-1-(1,3-dihydroxypropan-2-yl)-1H-indol-3-yl)-3-cycloheptylpropanamide

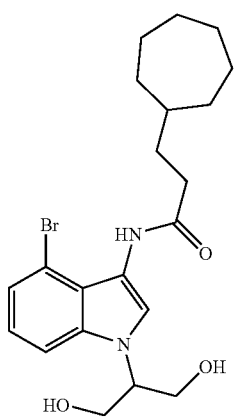

Synthesised according to the procedure disclosed in Example 22 where X is 4-bromo indole, Z is 2-cycloheptylpropionyl chloride. Formula: $C_{21}H_{29}BrN_2O_3$; Molecular Weight: 437.4; Mass/charge ratio: 438.1 (100.0%), 436.1 (99.4%), 437.1 (23.8%), 439.1 (23.4%), 440.1 (3.3%); Elemental analysis: C, 57.67; H, 6.68; Br, 18.27; N, 6.40; O, 10.97.

Example 42

N-(1-(3-amino-2-hydroxypropyl)-4-chloro-1H-indol-3-yl)-2-cyclohexylacetamide

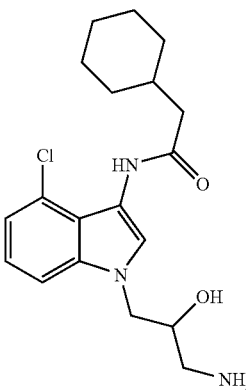

Synthesised according to the procedure disclosed in Example 23 where X is 4-chloro indole, Z is 2-cyclohexylacetyl chloride. Formula: $C_{19}H_{26}ClN_3O_2$; Molecular Weight: 363.9; Mass/charge ratio: 363.2 (100.0%), 365.2

(34.7%), 364.2 (22.0%), 366.2 (7.3%); Elemental analysis: C, 62.71; H, 7.20; Cl, 9.74; N, 11.55; O, 8.79.

Example 43

N-(1-(3-amino-2-hydroxypropyl)-4-bromo-1H-indol-3-yl)-2-cyclohexylacetamide

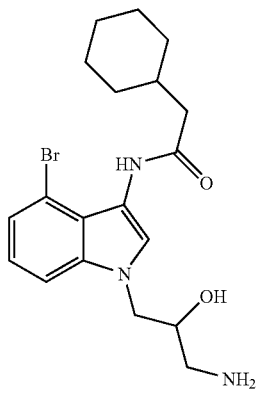

Synthesised according to the procedure disclosed in Example 23 where X is 4-bromo indole, Z is 2-cyclohexylacetyl chloride. Formula: $C_{19}H_{26}BrN_3O_2$; Molecular Weight: 408.3; Mass/charge ratio: 409.1 (100.0%), 407.1 (100.0%), 408.1 (22.0%), 410.1 (21.7%), 411.1 (2.7%); Elemental analysis: C, 55.89; H, 6.42; Br, 19.57; N, 10.29; O, 7.84.

Example 44

N-(1-(3-amino-2-hydroxypropyl)-4-chloro-1H-indol-3-yl)-2-cycloheptylacetamide

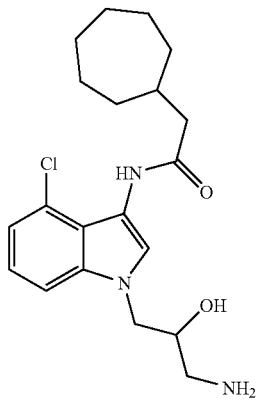

Synthesised according to the procedure disclosed in Example 23 where X is 4-chloro indole, Z is 2-cycloheptylacetyl chloride. Formula: $C_{20}H_{28}ClN_3O_2$; Molecular Weight: 377.9; Mass/charge ratio: 377.2 (100.0%), 379.2

(34.9%), 378.2 (23.1%), 380.2 (7.7%); Elemental analysis: C, 63.56; H, 7.47; Cl, 9.38; N, 11.12; O, 8.47.

Example 45

N-(1-(3-amino-2-hydroxypropyl)-4-bromo-1H-indol-3-yl)-2-cycloheptylacetamide

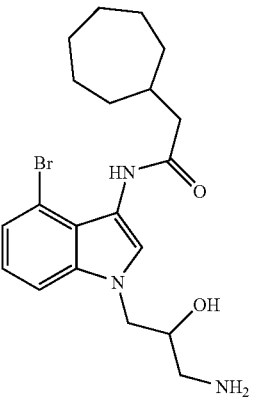

Synthesised according to the procedure disclosed in Example 23 where X is 4-bromo indole, Z is 2-cycloheptylacetyl chloride. Formula: $C_{20}H_{28}BrN_3O_2$; Molecular Weight: 422.4; Mass/charge ratio: 423.1 (100.0%), 421.1 (99.8%), 422.1 (23.1%), 424.1 (22.7%), 425.1 (2.9%); Elemental analysis: C, 56.87; H, 6.68; Br, 18.92; N, 9.95; O, 7.58.

Example 46

N-(1-(3-amino-2-hydroxypropyl)-4-chloro-1H-indol-3-yl)-2-(bicyclo[2.2.2]octan-1-yl)acetamide

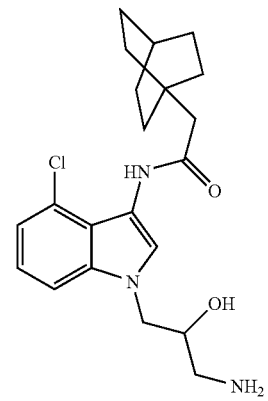

Synthesised according to the procedure disclosed in Example 23 where X is 4-chloro indole, Z is bicyclo[2.2.2]octan-1-yl acetyl chloride. Formula: $C_{21}H_{28}ClN_3O_2$; Molecular Weight: 389.9; Mass/charge ratio: 389.2

(100.0%), 391.2 (35.2%), 390.2 (24.2%), 392.2 (8.0%), 393.2 (1.1%); Elemental analysis: C, 64.69; H, 7.24; Cl, 9.09; N, 10.78; O, 8.21.

Example 47

N-(1-(3-amino-2-hydroxypropyl)-4-bromo-1H-indol-3-yl)-2-(bicyclo[2.2.2]octan-1-yl)acetamide

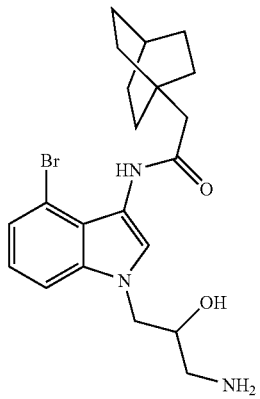

Synthesised according to the procedure disclosed in Example 23 where X is 4-bromo indole, Z is bicyclo[2.2.2]octan-1-yl acetyl chloride. Formula: $C_{21}H_{28}BrN_3O_2$; Molecular Weight: 434.4; Mass/charge ratio: 435.1 (100.0%), 433.1 (99.5%), 434.1 (24.1%), 436.1 (23.7%), 437.1 (3.1%); Elemental analysis: C, 58.07; H, 6.50; Br, 18.40; N, 9.67; O, 7.37.

Example 48

N-(1-(3-amino-2-hydroxypropyl)-4-chloro-1H-indol-3-yl)-3-cyclohexylpropanamide

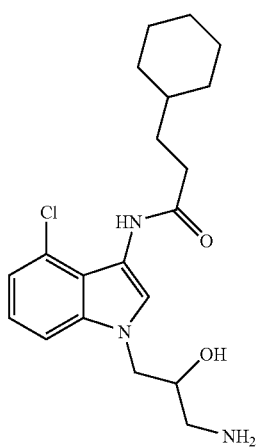

Synthesised according to the procedure disclosed in Example 23 where X is 4-chloro indole, Z is 2-cyclohexylpropionyl chloride. Formula: $C_{20}H_{28}ClN_3O_2$; Molecular Weight: 377.9; Mass/charge ratio: 377.2 (100.0%), 379.2 (34.9%), 378.2 (23.1%), 380.2 (7.7%); Elemental analysis: C, 63.56; H, 7.47; Cl, 9.38; N, 11.12; O, 8.47.

Example 49

N-(1-(3-amino-2-hydroxypropyl)-4-bromo-1H-indol-3-yl)-3-cyclohexylpropanamide

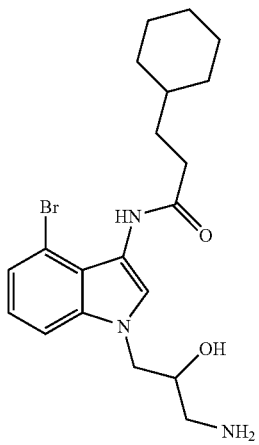

Synthesised according to the procedure disclosed in Example 23 where X is 4-bromo indole, Z is 2-cyclohexylpropionyl chloride. Formula: $C_{20}H_{28}BrN_3O_2$; Molecular Weight: 422.4; Mass/charge ratio: 423.1 (100.0%), 421.1 (99.8%), 422.1 (23.1%), 424.1 (22.7%), 425.1 (2.9%); Elemental analysis: C, 56.87; H, 6.68; Br, 18.92; N, 9.95; O, 7.58.

Example 50

N-(1-(3-amino-2-hydroxypropyl)-4-chloro-1H-indol-3-yl)-3-cycloheptylpropanamide

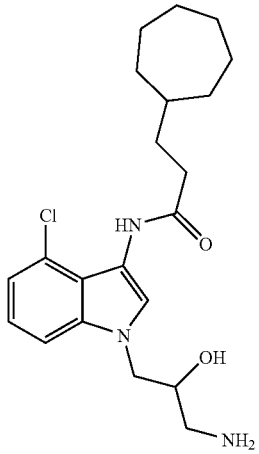

Synthesised according to the procedure disclosed in Example 23 where X is 4-chloro indole, Z is 2-cycloheptylpropionyl chloride. Formula: $C_{21}H_{30}ClN_3O_2$; Molecular Weight: 391.9; Mass/charge ratio: 391.2 (100.0%), 393.2

(35.2%), 392.2 (24.2%), 394.2 (8.1%), 395.2 (1.1%); Elemental analysis: C, 64.35; H, 7.72; Cl, 9.05; N, 10.72; O, 8.16.

Example 51

N-(1-(3-amino-2-hydroxypropyl)-4-bromo-1H-indol-3-yl)-3-cycloheptylpropanamide

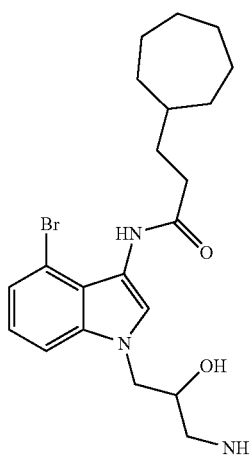

Synthesised according to the procedure disclosed in Example 23 where X is 4-bromo indole, Z is 2-cycloheptylpropionyl chloride. Formula: $C_{21}H_{30}BrN_3O_2$; Molecular Weight: 436.4; Mass/charge ratio: 437.2 (100.0%), 435.2 (99.5%), 436.2 (23.0%), 438.2 (22.7%), 439.2 (3.1%), 436.1 (1.1%), 438.1 (1.1%); Elemental analysis: C, 57.80; H, 6.93; Br, 18.31; N, 9.63; O, 7.33.

Example 52

N-(4-chloro-1-methyl-1H-indol-3-yl)-2-cyclohexylacetamide

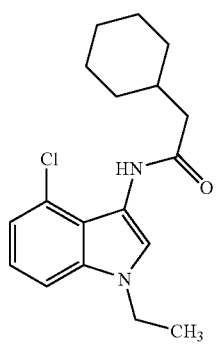

Synthesised according to the procedure disclosed in Example 20 where X is 4-chloro indole, Z is 2-cyclohexylacetyl chloride. Formula: $C_{17}H_{21}ClN_2O$; Molecular Weight: 304.8; Mass/charge ratio: 304.1 (100.0%), 306.1 (33.9%), 305.1 (19.4%), 307.1 (6.3%); Elemental analysis: C, 66.99; H, 6.94; Cl, 11.63; N, 9.19; O, 5.25.

Example 53

N-(4-bromo-1-methyl-1H-indol-3-yl)-2-cyclohexylacetamide

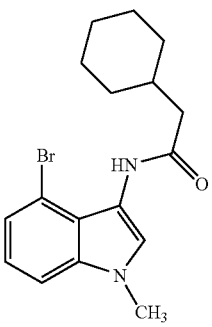

Synthesised according to the procedure disclosed in Example 20 where X is 4-bromo indole, Z is 2-cyclohexylacetyl chloride. Formula: $C_{17}H_{21}BrN_2O$; Molecular Weight: 349.3; Mass/charge ratio: 348.1 (100.0%), 350.1 (99.3%), 349.1 (19.4%), 351.1 (19.0%), 352.1 (1.9%); Elemental analysis: C, 58.46; H, 6.06; Br, 22.88; N, 8.02; O, 4.58.

Example 54

N-(4-chloro-1-methyl-1H-indol-3-yl)-2-cycloheptylacetamide

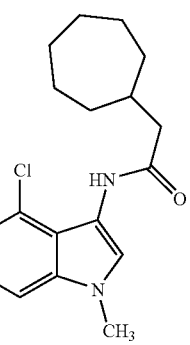

Synthesised according to the procedure disclosed in Example 20 where X is 4-chloro indole, Z is 2-cycloheptylacetyl chloride. Formula: $C_{18}H_{23}ClN_2O$; Molecular Weight: 318.8; Mass/charge ratio: 318.1 (100.0%), 320.1 (32.0%), 319.2 (19.8%), 321.2 (6.5%), 320.2 (2.2%); Elemental analysis: C, 67.81; H, 7.27; Cl, 11.12; N, 8.79; O, 5.02.

Example 55

N-(4-bromo-1-methyl-1H-indol-3-yl)-2-cycloheptylacetamide

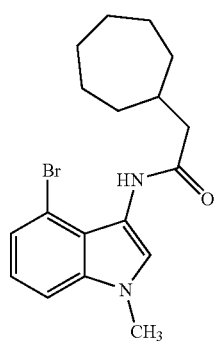

Synthesised according to the procedure disclosed in Example 20 where X is 4-bromo indole, Z is 2-cycloheptylacetyl chloride. Formula: $C_{18}H_{23}BrN_2O$; Molecular Weight: 363.3; Mass/charge ratio: 362.1 (100.0%), 364.1 (99.5%), 363.1 (20.5%), 365.1 (20.1%), 366.1 (2.2%); Elemental analysis: C, 59.51; H, 6.38; Br, 21.99; N, 7.71; O, 4.40.

Example 56

2-(bicyclo[2.2.2]octan-1-yl)-N-(4-chloro-1-methyl-1H-indol-3-yl)acetamide

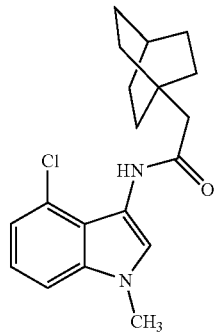

Synthesised according to the procedure disclosed in Example 20 where X is 4-chloro indole, Z is bicyclo[2.2.2]octan-1-yl acetyl chloride. Formula: $C_{19}H_{23}ClN_2O$; Molecular Weight: 330.9; Mass/charge ratio: 330.1 (100.0%), 332.1 (32.0%), 331.2 (20.9%), 333.2 (6.9%), 332.2 (2.4%); Elemental analysis: C, 68.97; H, 7.01; Cl, 10.72; N, 8.47; O, 4.84.

Example 57

2-(bicyclo[2.2.2]octan-1-yl)-N-(4-bromo-1-methyl-1H-indol-3-yl)acetamide

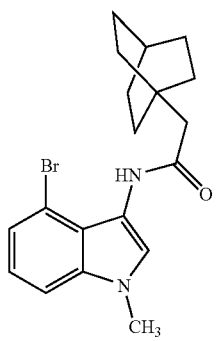

Synthesised according to the procedure disclosed in Example 20 where X is 4-bromo indole, Z is bicyclo[2.2.2]octan-1-yl acetyl chloride. Formula: $C_{19}H_{23}BrN_2O$; Molecular Weight: 375.3; Mass/charge ratio: 374.1 (100.0%), 376.1 (99.7%), 375.1 (21.6%), 377.1 (21.2%), 378.1 (2.4%); Elemental analysis: C, 60.81; H, 6.18; Br, 21.29; N, 7.46; O, 4.26.

Example 58

N-(4-chloro-1-methyl-1H-indol-3-yl)-3-cyclohexylpropanamide

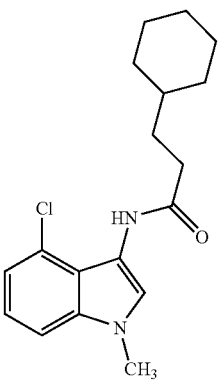

Synthesised according to the procedure disclosed in Example 20 where X is 4-chloro indole, Z is 2-cyclohexylpropionyl chloride. Formula: $C_{18}H_{23}ClN_2O$; Molecular Weight: 318.8; Mass/charge ratio: 318.1 (100.0%), 320.1

(32.0%), 319.2 (19.8%), 321.2 (6.5%), 320.2 (2.2%); Elemental analysis: C, 67.81; H, 7.27; Cl, 11.12; N, 8.79; O, 5.02.

Example 59

N-(4-bromo-1-methyl-1H-indol-3-yl)-3-cyclohexyl-propanamide

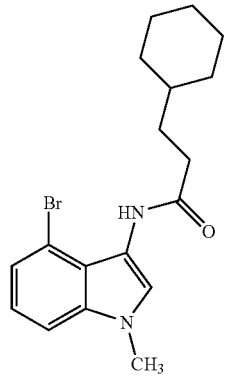

Synthesised according to the procedure disclosed in Example 20 where X is 4-bromo indole, Z is 2-cyclohexyl-propionyl chloride. Formula: $C_{18}H_{23}BrN_2O$; Molecular Weight: 363.3; Mass/charge ratio: 362.1 (100.0%), 364.1 (99.5%), 363.1 (20.5%), 365.1 (20.1%), 366.1 (2.2%); Elemental analysis: C, 59.51; H, 6.38; Br, 21.99; N, 7.71; O, 4.40.

Example 60

N-(4-chloro-1-methyl-1H-indol-3-yl)-3-cycloheptyl-propanamide

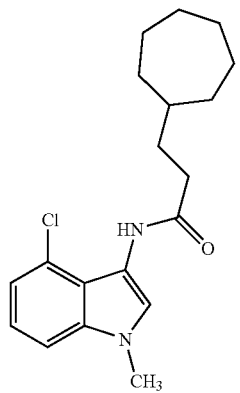

Synthesised according to the procedure disclosed in Example 20 where X is 4-chloro indole, Z is 2-cycloheptyl-propionyl chloride. Formula: $C_{19}H_{25}ClN_2O$; Molecular Weight: 332.9; Mass/charge ratio: 332.2 (100.0%), 334.2 (34.4%), 333.2 (21.6%), 335.2 (7.1%); Elemental analysis: C, 68.56; H, 7.57; Cl, 10.65; N, 8.42; O, 4.81.

Example 61

N-(4-bromo-1-methyl-1H-indol-3-yl)-3-cycloheptyl-propanamide

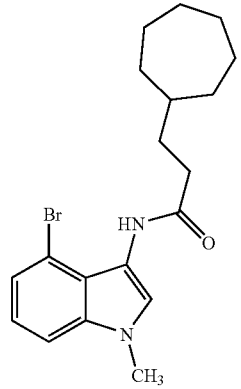

Synthesised according to the procedure disclosed in Example 20 where X is 4-bromo indole, Z is 2-cycloheptyl-propionyl chloride. Formula: $C_{19}H_{25}BrN_2O$; Molecular Weight: 377.3; Mass/charge ratio: 376.1 (100.0%), 378.1 (99.7%), 377.1 (21.6%), 379.1 (21.2%), 380.1 (2.4%); Elemental analysis: C, 60.48; H, 6.68; Br, 21.18; N, 7.42; O, 4.24.

Example 62

N-(4-chloro-1-(2-hydroxy-3-(methylamino)propyl)-1H-indol-3-yl)-2-cyclohexylacetamide

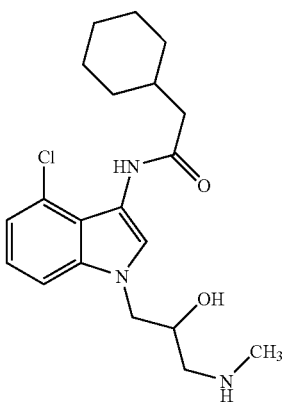

Synthesised according to the procedure disclosed in Example 23 where X is 4-chloro indole, Z is 2-cyclohexy-lacetyl chloride. Formula: $C_{20}H_{28}ClN_3O_2$; Molecular Weight: 377.9; Mass/charge ratio: 377.2 (100.0%), 379.2

(34.9%), 378.2 (23.1%), 380.2 (7.7%); Elemental analysis: C, 63.56; H, 7.47; Cl, 9.38; N, 11.12; O, 8.47.

Example 63

N-(4-bromo-1-(2-hydroxy-3-(methylamino)propyl)-1H-indol-3-yl)-2-cyclohexylacetamide

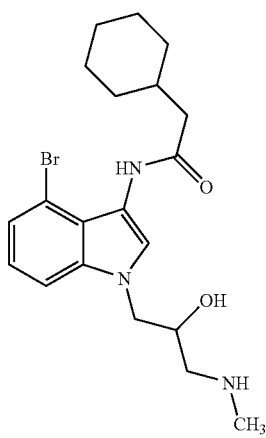

Synthesised according to the procedure disclosed in Example 23 where X is 4-bromo indole, Z is 2-cyclohexylacetyl chloride. Formula: $C_{20}H_{28}BrN_3O_2$; Molecular Weight: 422.4; Mass/charge ratio: 423.1 (100.0%), 421.1 (99.8%), 422.1 (23.1%), 424.1 (22.7%), 425.1 (2.9%); Elemental analysis: C, 56.87; H, 6.68; Br, 18.92; N, 9.95; O, 7.58.

Example 64

N-(4-chloro-1-(2-hydroxy-3-(methylamino)propyl)-1H-indol-3-yl)-2-cycloheptylacetamide

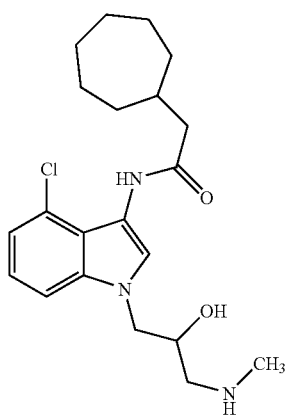

Synthesised according to the procedure disclosed in Example 23 where X is 4-chloro indole, Z is 2-cycloheptylacetyl chloride. Formula: $C_{21}H_{30}ClN_3O_2$; Molecular Weight: 391.9; Mass/charge ratio: 391.2 (100.0%), 393.2 (35.2%), 392.2 (24.2%), 394.2 (8.1%), 395.2 (1.1%); Elemental analysis: C, 64.35; H, 7.72; Cl, 9.05; N, 10.72; O, 8.16.

Example 65

N-(4-bromo-1-(2-hydroxy-3-(methylamino)propyl)-1H-indol-3-yl)-2-cycloheptylacetamide

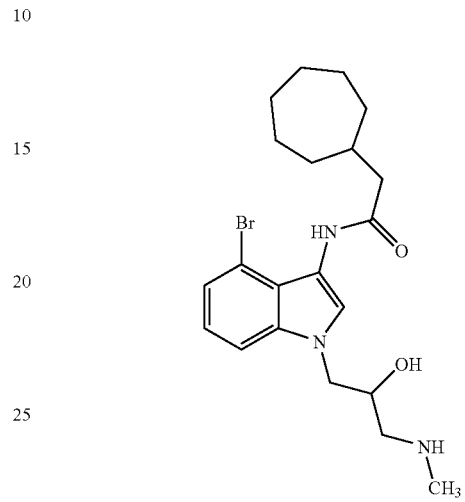

Synthesised according to the procedure disclosed in Example 23 where X is 4-bromo indole, Z is 2-cycloheptylacetyl chloride. Formula: $C_{21}H_{30}BrN_3O_2$; Molecular Weight: 436.4; Mass/charge ratio: 437.2 (100.0%), 435.2 (99.5%), 436.2 (23.0%), 438.2 (22.7%), 439.2 (3.1%), 436.1 (1.1%), 438.1 (1.1%); Elemental analysis: C, 57.80; H, 6.93; Br, 18.31; N, 9.63; O, 7.33.

Example 66

2-(bicyclo[2.2.2]octan-1-yl)-N-(4-chloro-1-(2-hydroxy-3-(methylamino)propyl)-H-indol-3-yl)acetamide

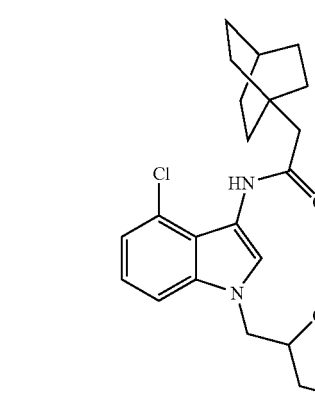

Synthesised according to the procedure disclosed in Example 23 where X is 4-chloro indole, Z is bicyclo[2.2.2]octan-1-yl acetyl chloride. Formula: $C_{22}H_{30}ClN_3O_2$; Molecular Weight: 403.9; Mass/charge ratio: 403.2

(100.0%), 405.2 (35.4%), 404.2 (25.3%), 406.2 (8.4%), 407.2 (1.1%); Elemental analysis: C, 65.41; H, 7.49; Cl, 8.78; N, 10.40; O, 7.92.

Example 67

2-(bicyclo[2.2.2]octan-1-yl)-N-(4-bromo-1-(2-hydroxy-3-(methylamino)propyl)-H-indol-3-yl)acetamide

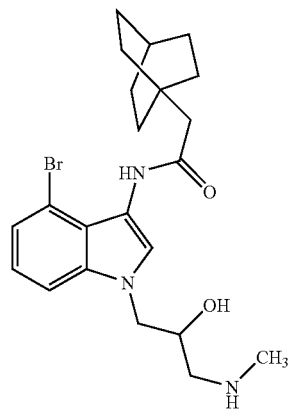

Synthesised according to the procedure disclosed in Example 23 where X is 4-bromo indole, Z is bicyclo[2.2.2]octan-1-yl acetyl chloride. Formula: $C_{22}H_{30}BrN_3O_2$; Molecular Weight: 448.4; Mass/charge ratio: 449.2 (100.0%), 447.2 (99.2%), 448.2 (24.0%), 450.2 (23.7%), 451.2 (3.4%), 448.1 (1.1%), 450.1 (1.1%); Elemental analysis: C, 58.93; H, 6.74; Br, 17.82; N, 9.37; O, 7.14.

Example 68

N-indol-3-yl-acetamide and N-azaindol-3-yl-acetamide compounds antagonise P2X7R activity Inhibition of P2X7R activity by the compounds of the present invention is assessed by measuring calcium influx in Hek293 cells (ECACC No. 85120602) which have been stably transfected with a cDNA for the human P2X7R.

The Hek293 cells are human embryo kidney cells that do not express endogenous P2X7R (Surprenant et al. (1996) Science 272:735-738). Hek293 cells expressing P2X7R were generated by lipofectamine transfection of the human P2X7R cDNA (Genbank accession number BC011913) under the control of the human cytomegalovirus immediate-early (CMV) promoter and inserted into the pcDNA3.1 vector (Invitrogen). Cells were cultivated at 37° C. with 8.5% $CO_2$ in Dulbecco's modified eagles medium (DMEM; GibcoBRL/Invitrogen) supplemented with heat-inactivated foetal calf serum (10% v/v), 2 mM L-glutamine, 100 units/ml penicillin, 0.1 mg/ml streptomycin, and 750 µg/ml Geneticin G418 (GibcoBRL/Invitrogen).

Inhibition of Bz-ATP-stimulated P2X7R by test compounds was monitored by measuring changes in calcium influx using the Fluo-4-AM fluorescent dye according to the manufacturer's recommendations (Molecular Devices Corporation, U.S.A.). Briefly, Hek293 cells expressing P2X7R were cultured in 96-well plates at a final density of approximately 10,000 cells per well. On the day of the experiment, the culture medium was completely removed from the wells and cells were washed one time in assay buffer (1×Hank's Balanced Salt (HBSS) solution containing 20 mM Hepes buffer pH 7.4 and 250 mM Probenecid; GibcoBRL/Invitrogen). The cells were incubated in 50 µl of assay buffer containing 100 µM Fluo-4 AM fluorescent dye per well for 1 hour at room temperature. The assay buffer containing the Fluo-4 AM fluorescent dye was then removed, the cells were washed once with assay buffer (without Fluo-4 AM), 100 µl of assay buffer (without Fluo-4 AM) containing the test compounds was then added per well. After a 15 minute incubation, 100 µM Bz-ATP was added and fluorescence was measured in a FlexStation II (Molecular Devices, U.S.A.) according to the following parameters: 485 nm Excitation Wavelength; 525 nm Emission Wavelength; 515 nm Emission Cut-off; 100 µl Pipette Height; 25 µl Transfer Volume; 5 fold Compound Concentration; 3 rate Addition Speed. Test compounds were added at concentrations of 0.001 µM up to 60 µM. The fluorescence data were processed using a lag time of 15 seconds, recording 45 seconds, zero baseline calibrated using 2 points, and % baseline multiplier set at 3. Then, the area of the resulting curve was calculated and the half-maximal inhibitory concentration (IC50) for each test compound was determined using SoftMax Pro software (Molecular Devices, U.S.A.). Compounds of the present invention can inhibit P2X7R activity with an IC50 between 1 µM and 0.001 µM. For example, the IC50 of compound described in Example 2 is approximately 0.0038 µM.

Example 69

N-indol-3-yl-acetamide and N-azaindol-3-yl-acetamide compounds reduce interleukin-1 beta secretion The effects of compounds of the present invention on IL-1 beta secretion is assessed using isolated human monocytes.

Briefly, human monocytes were purified from human blood by Ficoll-Paque from Buffy coats as follows. The Buffy coat is a greyish white layer of white blood cells and platelets that accumulates on the surface of sedimented erythrocytes when blood is allowed to stand or is centrifuged. Each Buffy coat (one per donor) was diluted with PBS and 20 ml added on top of 15 ml of Ficoll-Paque. The gradient was centrifuged at 900 g for 20 min at room temperature. The white interphase was transferred to a new tube, washed 3 times with PBS with three centrifugation steps (600, 400, 250 g), 10 min each, at room temperature. The cell pellet of Peripheral Blood Mononuclear Cells (PBMC) was resuspended (1×107 cells/mL) in RPMI 1640 supplemented with 5% heat-inactivated human serum. The resulting PBMC suspension contains monocytes and lymphocytes. The monocytes were let to adhere for 24 h at 37° C., 5% CO2 and the non-adherent lymphocytes were washed away with PBS. The PBMC differentiated into macrophages within 5 days of incubation at 37° C., 5% CO2. At day 5, the cells were counted, resuspended in RPMI 1640 supplemented with 5% human serum at a concentration of 1×106/ml and plated onto a 24 wells plate (5×105 cells/well). At day 6, medium was removed and replaced with RPMI 1640 supplemented with 10% heat-inactivated fetal bovine serum to avoid IL-1β contamination from the human serum.

The day of experiment, the macrophages were pre-stimulated for 2 hours with 1 µg/mL LPS at 37° C. Then 100 µM BzATP were added to the cells and incubated for 30 minutes at 37° C. AFC-5128 (see figures for concentrations) was added 5 minutes before the stimulation with BzATP. Control samples corresponded to the cells without any treatment. After incubation, the supernatants were collected by centrifugation (250 g for 5 minutes) and IL-1β secretion was measured by using the human IL-1 beta/IL-1F2 Quantikine ELISA Kit following manufacturer's instructions. Several donors were tested separately for AFC-5128. Each donor was tested in triplicates for each treatment. The O.D. at 450 nm was measured for each data points and the IL-11 concentration calculated based on a standard curve. The IL1β concentration was further calculated to have a concentration in pg/mL/10E+6 cells, together with its standard deviation.

An example of reduced IL-1beta secretion by the compounds of the invention is illustrated (in this case, the compound described in Example 2) in FIG. 1.

Example 70

Analgesic and Anti-inflammatory Effects

This example illustrates the analgesic and anti-inflammatory benefits of the compounds of the present invention using a carrageenan-induced paw edema model of inflammation.

Adult male Sprague Dawley rats were challenged by a subcutaneous injection of carrageenan (1% suspension, 0.1 ml), in the plantar side of the right hind paw. A suspension of the compound in 0.5% methyl cellulose or a vehicle (0.5% methyl cellulose) was administered orally one hour after the carrageenan challenge. The paw was then marked with indelible ink at the level of the lateral malleolus so that the paw can be immersed in the Plethysmometer cell up to this mark. A Plethysmometer allows the measurements of small volume changes in the paw. An hour after compound or vehicle administration (or 2 hr of carrageenan challenge), the plantar test was performed followed by the recording of paw volume.

For the plantar test, each rat was place on preheated glass stand. Both of the hind paws of the animal were stimulated with a radiant heat source. The latency of paw withdrawal from the stimuli was recorded. An increase in the response latency of paw withdrawal is interpreted as an analgesic response. Three trials were given to each animal in order to obtain an average withdrawal latency. The mean Paw Withdrawal Latency (PWL) of test group was compared with the vehicle treated group.

Figure 2:
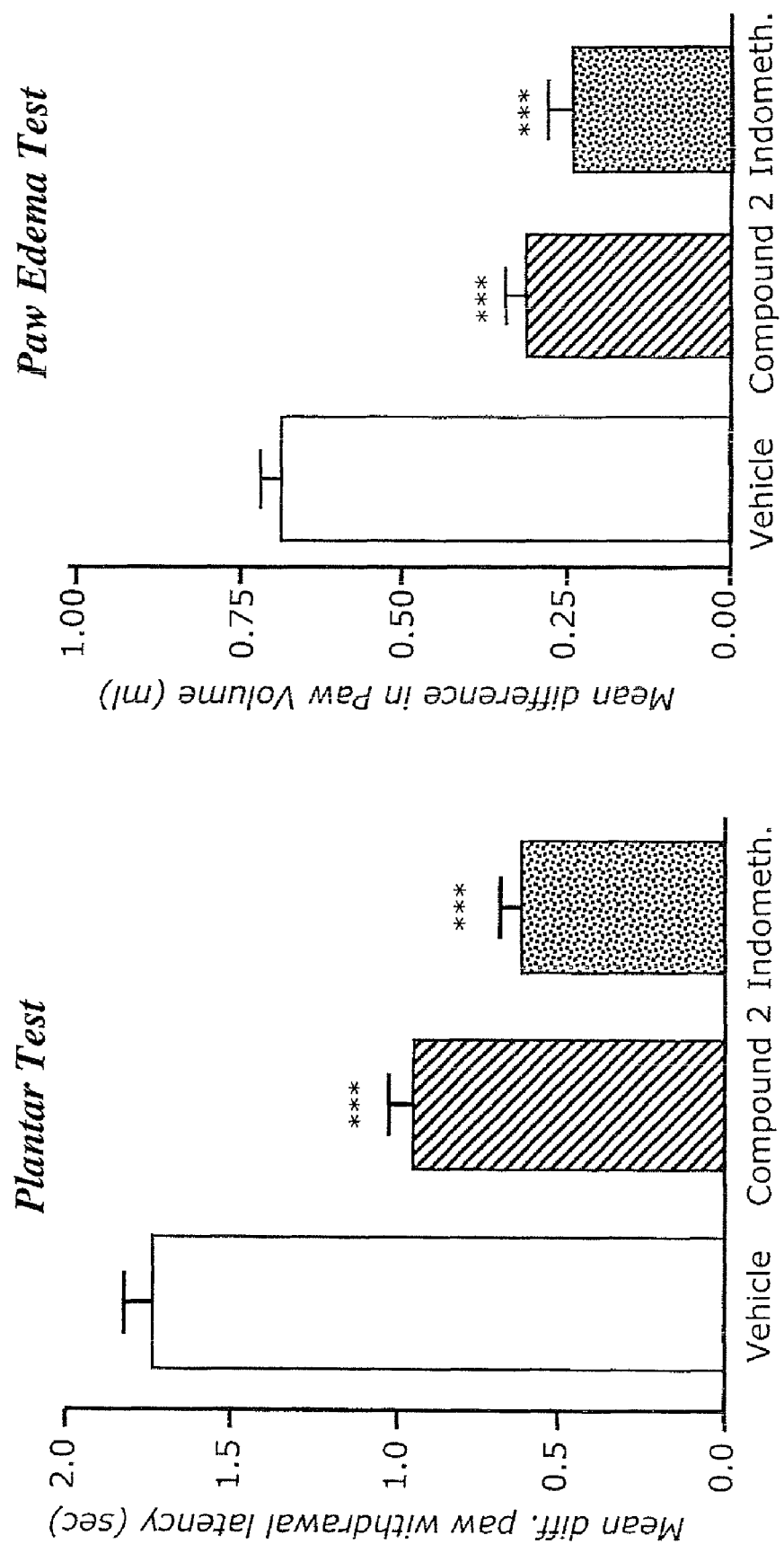
FIG. 2 discloses data showing analgesic and anti-inflammatory effects on a model of inflammation (** p<0.001) by compounds of the invention.

For the paw edema test, the increase in paw volume for each animal is calculated by subtracting left hind paw volume from right hind paw volume (Difference in Paw Volume=Right Hind paw volume−Left hind paw volume). An inhibition of the increase in paw volume is interpreted as an anti inflammatory response. Observed results were verified statistically using ANOVA Tukey's multiple comparison tests. Results are illustrated in FIG. 2.

A compound of the present invention (the compound described in Example 2) was evaluated for increase in the paw withdrawal latency to respond to the heat stimulus which is indicative of an analgesic response.

A compound of the present invention was also evaluated for inhibition of paw edema induced by carrageenan which is interpreted as an anti-inflammatory response.

The invention claimed is:
1. A compound of the general formula:

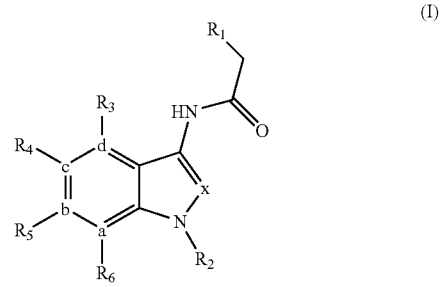

(I)

wherein,
$R_1$ is a mono- or bicycloalkylalkyl group or mono- or bicycloalkyl group;
$R_2$ is selected from straight or branched $C_1$-$C_5$ alkyl which may optionally substituted with —OH, —CH$_2$—OH, $C_1$-$C_5$ alkoxy, NH$_2$—, N(R$_a$)$_2$—, NHR$_a$—, CN—, CF$_3$, halogen (i.e. Cl, F, Br or I), piperidino, morpholino, pyrrolidino, 5H-tetrazolylpropyl, methylcarbamoyl, dimethylcarbamoyl, or ethylmethylcarbamoyl, wherein $R_a$ is $C_1$-$C_5$ alkyl;
$R_3$, $R_4$, $R_5$, $R_6$ are at each occurrence independently selected from hydrogen, halogen (i.e. Cl, F, Br or I), methyl, methoxy, cyano, or trifluoromethyl;
a, b, c, d, x are at each occurrence independently selected from carbon, or nitrogen; or a pharmaceutically acceptable salt thereof.

2. The compound according to claim 1, wherein $R_2$ is substituted with one or two substituents selected from —OH, —CH$_2$—OH, $C_1$-$C_5$ alkoxy, —NH$_2$, NHRa, —CN, —CF$_3$, halogen, piperidino, morpholino, pyrrolidino or 5H-tetrazolylpropyl.

3. The compound according to claim 1, wherein $R_1$ is a group selected from cyclopentyl, cyclopentylmethyl, cyclohexyl, cyclohexylmethyl, cycloheptyl, cycloheptylmethyl, bicyclo[2.2.2]octan-1-yl and bicyclo[2.2.2]octan-1-ylmethyl.

4. The compound according to claim 3, wherein $R_2$ is $C_1$-$C_5$ alkyl or $C_2$-$C_5$ hydroxyalkyl.

5. The compound according to claim 1, wherein at least two of $R_3$, $R_4$, $R_5$ and $R_6$ are hydrogen.

6. The compound according to claim 1, wherein x is CH.

7. The compound according to claim 1, wherein x is N.

8. The compound according to claim 1, wherein a, b, c, and d are C.

9. The compound according to claim 1, wherein one of a, b, c and d is N.

10. The compound according to claim 1 selected from the group consisting of:
N-(4-chloro-1-(2-hydroxyethyl)-1H-indol-3-yl)-2-cycloheptylacetamide,
N-(4-bromo-1-(2-hydroxyethyl)-1H-indol-3-yl)-2-cycloheptylacetamide,
N-(4-chloro-1-(2-hydroxyethyl)-1H-indol-3-yl)-2-cyclohexylacetamide,
N-(4-bromo-1-(2-hydroxyethyl)-1H-indol-3-yl)-2-cyclohexylacetamide,
N-(4-chloro-1-(2-hydroxypropyl)-1H-indol-3-yl)-2-cycloheptylacetamide,
N-(4-bromo-1-(2-hydroxypropyl)-1H-indol-3-yl)-2-cycloheptylacetamide,
N-(4-chloro-1-(hydroxymethyl)-1H-indol-3-yl)-3-cyclohexylpropanamide, N-(4-bromo-1-(hydroxymethyl)-1H-indol-3-yl)-3-cyclohexylpropanamide,
N-(4-chloro-1-(hydroxymethyl)-1H-indol-3-yl)-3-cycloheptylpropanamide,
N-(4-bromo-1-(hydroxymethyl)-1H-indol-3-yl)-3-cycloheptylpropanamide,
N-(4-chloro-1-(2-hydroxyethyl)-1H-pyrrolo[2,3-b]pyridin-3-yl)-2-cyclohexylacetamide,
N-(4-bromo-1-(2-hydroxyethyl)-1H-pyrrolo[2,3-b]pyridin-3-yl)-2-cyclohexylacetamide,
N-(4-chloro-1-(2-hydroxyethyl)-1H-pyrrolo[2,3-b]pyridin-3-yl)-2-cycloheptylacetamide,
N-(4-bromo-1-(2-hydroxyethyl)-1H-pyrrolo[2,3-b]pyridin-3-yl)-2-cycloheptylacetamide,
N-(4-chloro-1-(2-hydroxypropyl)-1H-pyrrolo[2,3-b]pyridin-3-yl)-2-cycloheptylacetamide,
N-(4-bromo-1-(2-hydroxypropyl)-1H-pyrrolo[2,3-b]pyridin-3-yl)-2-cycloheptylacetamide,
N-(4-chloro-1-(2-hydroxyethyl)-1H-pyrrolo[2,3-b]pyridin-3-yl)-3-cyclohexylpropanamide,
N-(4-bromo-1-(2-hydroxyethyl)-1H-pyrrolo[2,3-b]pyridin-3-yl)-3-cyclohexylpropanamide,
N-(4-chloro-1-(2-hydroxypropyl)-1H-indol-3-yl)-2-cyclohexylacetamide,
N-(4-bromo-1-(2-hydroxypropyl)-1H-indol-3-yl)-2-cyclohexylacetamide,
2-(bicyclo[2.2.2]octan-1-yl)-N-(4-chloro-1-(2-hydroxypropyl)-1H-indol-3-yl)acetamide,
2-(bicyclo[2.2.2]octan-1-yl)-N-(4-bromo-1-(2-hydroxypropyl)-1H-indol-3-yl)acetamide,
N-(4-chloro-1-(2-hydroxypropyl)-1H-indol-3-yl)-3-cyclohexylpropanamide,
N-(4-bromo-1-(2-hydroxypropyl)-1H-indol-3-yl)-3-cyclohexylpropanamide,
N-(4-chloro-1-(2-hydroxypropyl)-1H-indol-3-yl)-3-cycloheptylpropanamide,
N-(4-bromo-1-(2-hydroxypropyl)-1H-indol-3-yl)-3-cycloheptylpropanamide,
N-(4-chloro-1-(1,3-dihydroxypropan-2-yl)-1H-indol-3-yl)-2-cyclohexylacetamide,
N-(4-bromo-1-(1,3-dihydroxypropan-2-yl)-1H-indol-3-yl)-2-cyclohexylacetamide,
N-(4-chloro-1-(1,3-dihydroxypropan-2-yl)-1H-indol-3-yl)-2-cycloheptylacetamide,
N-(4-bromo-1-(1,3-dihydroxypropan-2-yl)-1H-indol-3-yl)-2-cycloheptylacetamide,
2-(bicyclo[2.2.2]octan-1-yl)-N-(4-chloro-1-(1,3-dihydroxypropan-2-yl)-1H-indol-3-yl)acetamide
2-(bicyclo[2.2.2]octan-1-yl)-N-(4-bromo-1-(1,3-dihydroxypropan-2-yl)-1H-indol-3-yl)acetamide,
N-(4-chloro-1-(1,3-dihydroxypropan-2-yl)-1H-indol-3-yl)-3-cyclohexylpropanamide,
N-(4-bromo-1-(1,3-dihydroxypropan-2-yl)-1H-indol-3-yl)-3-cyclohexylpropanamide,
N-(4-chloro-1-(1,3-dihydroxypropan-2-yl)-1H-indol-3-yl)-3-cycloheptylpropanamide,
N-(4-bromo-1-(1,3-dihydroxypropan-2-yl)-1H-indol-3-yl)-3-cycloheptylpropanamide,
N-(1-(3-amino-2-hydroxypropyl)-4-chloro-1H-indol-3-yl)-2-cyclohexylacetamide,
N-(1-(3-amino-2-hydroxypropyl)-4-bromo-1H-indol-3-yl)-2-cyclohexylacetamide,
N-(1-(3-amino-2-hydroxypropyl)-4-chloro-1H-indol-3-yl)-2-cycloheptylacetamide,
N-(1-(3-amino-2-hydroxypropyl)-4-bromo-1H-indol-3-yl)-2-cycloheptylacetamide,
N-(1-(3-amino-2-hydroxypropyl)-4-chloro-1H-indol-3-yl)-2-(bicyclo[2.2.2]octan-1-yl)acetamide,
N-(1-(3-amino-2-hydroxypropyl)-4-bromo-1H-indol-3-yl)-2-(bicyclo[2.2.2]octan-1-yl)acetamide,
N-(1-(3-amino-2-hydroxypropyl)-4-chloro-1H-indol-3-yl)-3-cyclohexylpropanamide,
N-(1-(3-amino-2-hydroxypropyl)-4-bromo-1H-indol-3-yl)-3-cyclohexylpropanamide,
N-(1-(3-amino-2-hydroxypropyl)-4-chloro-1H-indol-3-yl)-3-cycloheptylpropanamide,
N-(1-(3-amino-2-hydroxypropyl)-4-bromo-1H-indol-3-yl)-3-cycloheptylpropanamide,
N-(4-chloro-1-methyl-1H-indol-3-yl)-2-cyclohexylacetamide,
N-(4-bromo-1-methyl-1H-indol-3-yl)-2-cyclohexylacetamide,
N-(4-chloro-1-methyl-1H-indol-3-yl)-2-cycloheptylacetamide,
N-(4-bromo-1-methyl-1H-indol-3-yl)-2-cycloheptylacetamide,
2-(bicyclo[2.2.2]octan-1-yl)-N-(4-chloro-1-methyl-1H-indol-3-yl)acetamide,
2-(bicyclo[2.2.2]octan-1-yl)-N-(4-bromo-1-methyl-1H-indol-3-yl)acetamide,
N-(4-chloro-1-methyl-1H-indol-3-yl)-3-cyclohexylpropanamide,
N-(4-bromo-1-methyl-1H-indol-3-yl)-3-cyclohexylpropanamide,
N-(4-chloro-1-methyl-1H-indol-3-yl)-3-cycloheptylpropanamide,
N-(4-bromo-1-methyl-1H-indol-3-yl)-3-cycloheptylpropanamide,
N-(4-chloro-1-(2-hydroxy-3-(methylamino)propyl)-1H-indol-3-yl)-2-cyclohexylacetamide,
N-(4-bromo-1-(2-hydroxy-3-(methylamino)propyl)-1H-indol-3-yl)-2-cyclohexylacetamide,
N-(4-chloro-1-(2-hydroxy-3-(methylamino)propyl)-1H-indol-3-yl)-2-cycloheptylacetamide,
N-(4-bromo-1-(2-hydroxy-3-(methylamino)propyl)-1H-indol-3-yl)-2-cycloheptylacetamide,
2-(bicyclo[2.2.2]octan-1-yl)-N-(4-chloro-1-(2-hydroxy-3-(methylamino)propyl)-1H-indol-3-yl)acetamide, and
2-(bicyclo[2.2.2]octan-1-yl)-N-(4-bromo-1-(2-hydroxy-3-(methylamino)propyl)-1H-indol-3-yl)acetamide.

11. A pharmaceutical composition comprising a compound according to claim 1.

12. The pharmaceutical composition according claim 11, further comprising an additional active compound in separate or unit dosage form for simultaneous or sequential administration.

* * * * *